United States Patent [19]

Agrafiotis et al.

[11] Patent Number: 5,684,711
[45] Date of Patent: *Nov. 4, 1997

[54] SYSTEM, METHOD, AND COMPUTER PROGRAM FOR AT LEAST PARTIALLY AUTOMATICALLY GENERATING CHEMICAL COMPOUNDS HAVING DESIRED PROPERTIES

[75] Inventors: Dimitris K. Agrafiotis, Exton, Pa.; Roger F. Bone, Bridgewater, N.J.; Francis R. Salemme, Kennett Square, Pa.; Richard M. Soll, Lawrenceville, N.J.

[73] Assignee: 3-Dimensional Pharmaceuticals, Inc., Philadelphia, Pa.

[*] Notice: The term of this patent shall not extend beyond the expiration date of Pat. No. 5,463,564.

[21] Appl. No.: 698,246

[22] Filed: Aug. 15, 1996

Related U.S. Application Data

[63] Continuation of Ser. No. 535,822, Sep. 28, 1995, Pat. No. 5,574,656, which is a continuation of Ser. No. 306,915, Sep. 16, 1994, Pat. No. 5,463,564.

[51] Int. Cl.$^6$ ............................................. G06F 17/50
[52] U.S. Cl. .................. 364/500; 364/496; 436/43; 423/659; 424/2
[58] Field of Search ................. 364/496, 497, 364/500, 578; 436/43, 50, 55; 423/659; 424/2

[56] References Cited

U.S. PATENT DOCUMENTS

| | | | |
|---|---|---|---|
| 4,939,666 | 7/1990 | Hardman | 436/89 |
| 5,240,680 | 8/1993 | Zuckerman et al. | 422/67 |
| 5,270,170 | 12/1993 | Schatz et al. | 435/7.37 |
| 5,288,514 | 2/1994 | Ellman | 427/2 |
| 5,331,573 | 7/1994 | Balaji et al. | 364/500 |
| 5,463,564 | 10/1995 | Agrafiotis et al. | 364/496 |
| 5,574,656 | 11/1996 | Agrafiotis et al. | 364/500 |

FOREIGN PATENT DOCUMENTS

| | | |
|---|---|---|
| 0 355 628 | 10/1989 | European Pat. Off. |
| 0 355 266 | 2/1990 | European Pat. Off. |
| WO 91/19735 | 12/1991 | WIPO . |
| 92/00091 | 1/1992 | WIPO . |
| 93/20242 | 10/1993 | WIPO . |

OTHER PUBLICATIONS

"Applications of Combinatorial Technologies to Drug Discovery: Background and Peptide Combinatorial Libraries", *Journal of Medicinal Chemistry*, vol. 37, No. 9, pp. 1233–1250, 1994.

"Applications of Combinatorial Technologies to Drug Discovery: Combinatorial Organic Synthesis, Library Screening Strategies, and Future Directions", *Journal of Medicinal Chemistry*, vol. 37, No. 10, pp. 1385–1400, 1994.

(List continued on next page.)

*Primary Examiner*—Emanuel T. Voeltz
*Assistant Examiner*—Kyle J. Choi
*Attorney, Agent, or Firm*—Sterne, Kessler, Goldstein & Fox P.L.L.C.

[57] ABSTRACT

A computer based, iterative process for generating chemical entities with defined physical, chemical and/or bioactive properties. During each iteration of the process, (1) a directed diversity chemical library is robotically generated in accordance with robotic synthesis instructions; (2) the compounds in the directed diversity chemical library are analyzed to identify compounds with the desired properties; (3) structure-property data are used to select compounds to be synthesized in the next iteration; and (4) new robotic synthesis instructions are automatically generated to control the synthesis of the directed diversity chemical library for the next iteration.

54 Claims, 12 Drawing Sheets

OTHER PUBLICATIONS

"Combinatorial Approaches Provide Fresh Leads for Medicinal Chemistry", *C&EN*, Feb. 1994.

"Current Trends in Synthetic Peptide and Chemical Diversity Library Design", *Genetic Engineering News*, pp. 31–32, May 1, 1994.

Pabo et al., "Computer-Aided Model Building Strategies for Protein Design", *Biochemistry*, vol. 25, No. 20, pp. 5987–5991, 1986.

Saudek et al., "Solution Conformation of Endothelin-1 by H NMR, CD, and Molecular Modeling", *International Journal of Peptide Protein Res.*, No. 37, pp. 174–179, 1991.

"Screening Chemically Synthesized Peptide Libraries for Biologically-Relevent Molecules", *Organic & Medicinal Chemistry Letters*, vol. 3, p. 397–404, 1993.

"Strategies for Indirect Computer-Aided Drug Design", *Pharmaceutical Research*, vol. 10, No. 4, pp. 475–486, 1993.

"The Use of Synthetic Peptide Combinatorial Libraries for the Identification of Bioactive Peptides", *Peptide Research*, vol. 5, No. 6, pp. 351–358, 1992.

SYSTEM, METHOD, AND COMPUTER PROGRAM FOR AT LEAST PARTIALLY AUTOMATICALLY GENERATING CHEMICAL COMPOUNDS HAVING DESIRED PROPERTIES

This application is a continuation of application Ser. No. 08/535,822, filed Sep. 28, 1995, now U.S. Pat. No. 5,574,656, which is a Continuation application of application Ser. No. 08/306,915, filed Sep. 16, 1994, now U.S. Pat. No. 5,463,564.

BACKGROUND OF THE INVENTION

1. Field of the Invention

The present invention relates generally to the generation of chemical entities with defined physical, chemical or bioactive properties, and particularly to the automatic generation of drug leads via computer-based, iterative robotic synthesis and analysis of directed diversity chemical libraries.

2. Related Art

Conventionally, new chemical entities with useful properties are generated by identifying a chemical compound (called a "lead compound") with some desirable property or activity, creating variants of the lead compound, and evaluating the property and activity of those variant compounds. Examples of chemical entities with useful properties include paints, finishes, plasticizers, surfactants, scents, flavorings, and bioactive compounds, but can also include chemical compounds with any other useful property that depends upon chemical structure, composition, or physical state. Chemical entities with desirable biological activities include drugs, herbicides, pesticides, veterinary products, etc. There are a number of flaws with this conventional approach to lead generation, particularly as it pertains to the discovery of bioactive compounds.

One deficiency pertains to the first step of the conventional approach, i.e., the identification of lead compounds. Traditionally, the search for lead compounds has been limited to an analysis of compound banks, for example, available commercial, custom, or natural products chemical libraries. Consequently, a fundamental limitation of the conventional approach is the dependence upon the availability, size, and structural diversity of these chemical libraries. Although chemical libraries cumulatively total an estimated 9 million identified compounds, they reflect only a small sampling of all possible organic compounds with molecular weights less than 1200. Moreover, only a small subset of these libraries is usually accessible for biological testing. Thus, the conventional approach is limited by the relatively small pool of previously identified chemical compounds which may be screened to identify new lead compounds.

Also, compounds in a chemical library are traditionally screened (for the purpose of identifying new lead compounds) using a combination of empirical science and chemical intuition. However, as stated by Rudy M. Baum in his article "Combinatorial Approaches Provide Fresh Leads for Medicinal Chemistry," *C&EM*, Feb. 7, 1994, pages 20–26, "chemical intuition, at least to date, has not proven to be a particularly good source of lead compounds for the drug discovery process."

Another deficiency pertains to the second step of the conventional approach, i.e., the creation of variants of lead compounds. Traditionally, lead compound variants are generated by chemists using conventional chemical synthesis procedures. Such chemical synthesis procedures are manually performed by chemists. Thus, the generation of lead compound variants is very labor intensive and time consuming. For example, it typically takes many chemist years to produce even a small subset of the compound variants for a single lead compound. Baum, in the article referenced above, states that "medicinal chemists, using traditional synthetic techniques, could never synthesize all of the possible analogs of a given, promising lead compound" (emphasis added). Thus, the use of conventional, manual procedures for generating lead compound variants operates to impose a limit on the number of compounds that can be evaluated as new drug leads. Overall, the traditional approach to new lead generation is an inefficient, labor-intensive, time consuming process of limited scope.

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds theoretically can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., "Applications of Combinatorial Technologies to Drug Discovery, Background and Peptide Combinatorial Libraries," *Journal of Medicinal Chemistry*, Volume 37, Number 9, pages 1233–1250, Apr. 29, 1994).

To date, most work with combinatorial chemical libraries has been limited only to peptides and oligonucleotides for the purpose of identifying bioactive agents; little research has been performed using non-peptide, non-nucleotide based combinatorial chemical libraries. It has been shown that the compounds in peptide and oligonucleotide based combinatorial chemical libraries can be assayed to identify ones having bioactive properties. However, there is no consensus on how such compounds (identified as having desirable bioactive properties and desirable profile for medicinal use) can be used.

Some commentators speculate that such compounds could be used as orally efficacious drugs. This is unlikely, however, for a number of reasons. First, such compounds would likely lack metabolic stability. Second, such compounds would be very expensive to manufacture, since the chemical building blocks from which they are made most likely constitute high priced reagents. Third, such compounds would tend to have a large molecular weight, such that they would have bioavailability problems (i.e., they could only be taken by injection).

Others believe that the compounds from a combinatorial chemical library that are identified as having desirable biological properties could be used as lead compounds. Variants of these lead compounds could be generated and evaluated in accordance with the conventional procedure for generating new bioactive compound leads, described above. However, the use of combinatorial chemical libraries in this manner does not solve all of the problems associated with the conventional lead generation procedure. Specifically, the problem associated with manually synthesizing variants of the lead compounds is not resolved.

In fact, the use of combinatorial chemical libraries to generate lead compounds exacerbates this problem. Greater and greater diversity has often been achieved in combinatorial chemical libraries by using larger and larger compounds (that is, compounds having a greater number of variable subunits, such as pentameric compounds instead of tetrameric compounds in the case of polypeptides). However, it is more difficult, time consuming, and costly to synthesize variants of larger compounds. Furthermore, the real issues of structural and functional group diversity are still not directly addressed; bioactive agents such as drugs and agricultural products possess diversity that could never be achieved with available peptide and oligonucleotide libraries since the available peptide and oligonucleotide components only possess limited functional group diversity and limited topology imposed through the inherent nature of the available components. Thus, the difficulties associated with synthesizing variants of lead compounds are exacerbated by using typical peptide and oligonucleotide combinatorial chemical libraries to produce such lead compounds. The issues described above are not limited to bioactive agents but rather to any lead generating paradigm for which a chemical agent of defined and specific activity is desired.

Thus, the need remains for a system and method for efficiently and effectively generating new leads designed for specific utilities.

SUMMARY OF THE INVENTION

The present invention is directed to a computer based system and method for automatically generating chemical entities with desired physical, chemical and/or biological properties. The present invention is also directed to the chemical entities produced by this system and method. For purposes of illustration, the present invention is described herein with respect to the production of drug leads. However, the present invention is not limited to this embodiment.

Specifically, the present invention is directed to an iterative process for generating new chemical compounds with a prescribed set of physical, chemical and/or biological properties, and to a system for implementing this process. During each iteration of the process, (1) a directed diversity chemical library is robotically generated in accordance with robotic synthesis instructions; (2) the compounds in the directed diversity chemical library are analyzed under computer control, and structure-activity/structure-property models (collectively referred to as structure-activity models hereafter) are constructed and/or refined; and (3) new robotic synthesis instructions are generated to control the synthesis of the directed diversity chemical library for the next iteration.

More particularly, during each iteration of the process, the system of the present invention robotically synthesizes, in accordance with robotic synthesis instructions, a directed diversity chemical library comprising a plurality of chemical compounds. The chemical compounds are robotically analyzed to obtain structure-activity/structure-property data (collectively referred to as structure-activity data hereafter) pertaining thereto. The structure-activity data is stored in a structure-activity/structure-property database (referred to as structure-activity database hereafter). The structure-activity database also stores therein structure-activity data pertaining to previously synthesized compounds.

The system of the present invention evaluates, under computer control, the structure-activity data of the chemical compounds obtained from all previous iterations (or a subset of all previous iterations as specified by user input, for example) and constructs structure-activity models that substantially conform to the observed data.

The system of the present invention then identifies, under computer control, reagents, from a reagent database, which, when combined, will produce compounds which are predicted to (1) exhibit improved activity/properties, (2) test the validity of the current structure-activity models, and/or (3) discriminate between the various structure-activity models. Under the system of the present invention, a plurality of structure-activity models may be tested and evaluated in parallel.

Then, the system of the present invention generates, under computer control, new robotic synthesis instructions which, when executed, enable robotic synthesis of chemical compounds from selected combinations of the identified reagents. Such new robotic synthesis instructions are used to generate a new directed diversity chemical library during the next iteration.

Further features and advantages of the present invention, as well as the structure and operation of various embodiments of the present invention, are described in detail below with reference to the accompanying drawings. In the drawings, like reference numbers indicate identical or functionally similar elements. Also, the leftmost digit(s) of the reference numbers identify the drawings in which the associated elements are first introduced.

BRIEF DESCRIPTION OF THE FIGURES

The present invention will be described with reference to the accompanying drawings, wherein.

DETAILED DESCRIPTION OF THE PREFERRED EMBODIMENTS

1. General Overview

The present invention is directed to the computer-aided generation of chemical entities with a prescribed set of physical, chemical and/or bioactive properties via computer-based, iterative robotic synthesis and analysis of directed diversity chemical libraries. The present invention is also directed to the new chemical entities generated by operation of the present invention.

According to the present invention, a directed diversity chemical library is not the same as a combinatorial chemical library. As discussed above, a combinatorial chemical library comprises a plurality of chemical compounds which are formed by combining, in every possible way for a given compound length (i.e., the number of building blocks in a compound), a set of chemical building blocks. For example, suppose that three chemical building blocks (designated as A, B, and C) are used to generate a combinatorial chemical library. Also suppose that the length of the compounds in the combinatorial chemical library is equal to two. In this case, the following compounds would be generated: AA, AB, AC, BA, BB, BC, CA, CB, and CC.

In contrast, a directed diversity chemical library comprises a plurality of chemical compounds which are formed by selectively combining a particular set of chemical building blocks. Thus, whereas discovery using combinatorial chemical libraries tends to be scattershot and random (essentially constituting a "needle in a haystack" research paradigm), the use by the present invention of directed diversity chemical libraries results in an optimization approach which is focused and directed.

Figure 11:
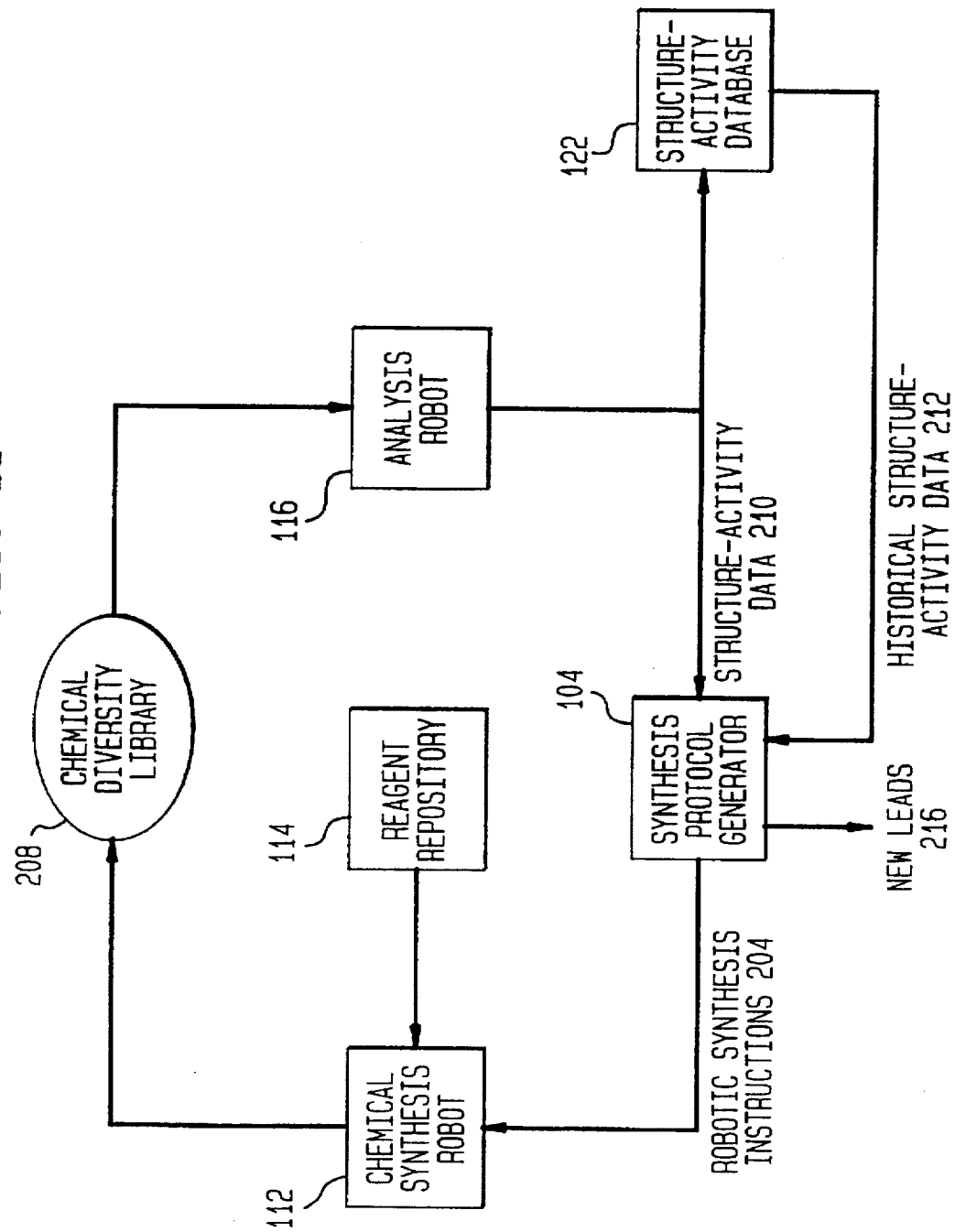
FIG. 11 is used to describe the preferred, high level operation of the present invention.

As shown in FIG. 11, the present invention includes a Chemical Synthesis Robot 112 which operates in accordance with robotic synthesis instructions 204 to synthesize a Directed Diversity Chemical Library 208. The Chemical Synthesis Robot 112 synthesizes the Directed Diversity Chemical Library 208 by selectively mixing a set of chemical building blocks from a Reagent Repository 114 in accordance with the robotic synthesis instructions 204.

In one example of the present invention, discussed here to generally illustrate the present invention, these chemical building blocks comprise approximately 100 commercially available reagents suitable for generating thrombin inhibitors. However, it should be understood that the present invention is not limited to this example. Preferably, the Chemical Synthesis Robot 112 combines these reagents using well known synthetic chemistry techniques to synthesize inhibitors of the enzyme thrombin. Each inhibitor is generally composed of, but not restricted to, three chemical building blocks. Thus, the Directed Diversity Chemical Library 208 preferably comprises a plurality of thrombin inhibitors generally composed of, but not restricted to, three sites of variable structure (i.e., trimers).

Again, however, it should be understood that the present invention is not limited to this thrombin example. The present invention is equally adapted and intended to generate chemical compounds (other than thrombin inhibitors) having other desired properties, such as paints, finishes, plasticizers, surfactants, scents, flavorings, bioactive compounds, drugs, herbicides, pesticides, veterinary products, etc., and/or lead compounds for any of the above. In fact, the present invention is adapted and intended to generate chemical compounds having any useful properties that depend upon structure, composition, or state.

Still referring to FIG. 11, the Directed Diversity Chemical Library 208 generated by the Chemical Synthesis Robot 112 is provided to an analysis robot 116. The analysis robot 116 analyzes (chemically, biochemically, physically, and/or biophysically) the compounds in the Directed Diversity Chemical Library 208 to obtain structure-activity/structure-property data (called herein Structure-Activity Data) 210 pertaining to the compounds. Such structure-activity/ structure-property data 210 includes well known structure-activity/structure property relationship data (collectively referred to as structure-activity relationships or SAR hereafter) pertaining to the relationship(s) between a compound's activity/properties and its chemical structure. Preferably, the analysis robot 116 assays the compounds in the Directed Diversity Chemical Library 208 to obtain, for example, enzyme activity data, cellular activity data, toxicology data, and/or bioavailability data pertaining to the compounds. Optionally, the analysis robot 116 also analyzes the compounds to identify which of the compounds were adequately synthesized, and which of the compounds were not adequately synthesized. This could be useful, since not all combinations of chemical building blocks may interact as expected. The analysis robot 116 further analyzes the compounds to obtain other pertinent data, such as data pertaining to the compounds' composition, structure and electronic structure.

This data obtained by the analysis robot 116 (i.e., physical data, synthesis data, enzyme activity data, cellular activity data, toxicology data, bioavailability data, etc.) collectively represents the Structure-Activity Data 210 shown in FIG. 11. The Structure-Activity Data 210 is stored in a Structure-Activity Database 122, and is provided to a Synthesis Protocol Generator 104.

The Synthesis Protocol Generator 104 uses the Structure-Activity Data 210 of the chemical compounds in the Directed Diversity Chemical Library 208, as well as historical structure-activity data 212 pertaining to chemical compounds that were previously synthesized (or known), to derive and/or refine structure-activity models that substantially conform to the observed data.

The synthesis protocol generator then identifies, under computer control, reagents, from a Reagent Repository 114, which, when combined with each other, will produce compounds which are predicted (by the structure-activity models) to (1) exhibit improved activity/properties, (2) test the validity of the current structure-activity models, and/or (3) discriminate between the various structure-activity models. Under the system of the present invention, one or more structure-activity models may be tested and evaluated in parallel.

In addition, the Synthesis Protocol Generator 104 classifies any compounds which possess the desired activity/ properties as new leads (lead compounds) 216.

After performing this analysis, the Synthesis Protocol Generator 104 generates new robotic synthesis instructions 204 which pertain to the synthesis of chemical compounds from combinations of the identified reagents. These new robotic synthesis instructions 204 are provided to the Chemical Synthesis Robot 112.

Then, the process described above is repeated. In particular, the Chemical Synthesis Robot 112 operates in accordance with the new robotic synthesis instructions 204 to synthesize a new Directed Diversity Chemical Library 208 by selectively combining the identified reagents. The analysis robot 116 analyzes the new Directed Diversity Chemical Library 208 to obtain Structure-Activity Data 210 pertaining to the compounds in the new Directed Diversity Chemical Library 208. The Synthesis Protocol Generator 104 analyzes the Structure-Activity Data 210 pertaining to the compounds in the new Directed Diversity Chemical Library 208 to improve the structure-activity models, and to generate new robotic synthesis instructions 204.

Thus, the present invention is an iterative process for generating new chemical entities having a set of physical, chemical and/or biological properties optimized towards a prescribed target. During each iteration, a Directed Diversity Chemical Library 208 is generated, the compounds in the Directed Diversity Chemical Library 208 are analyzed, structure-activity models are derived and elaborated, and robotic synthesis instructions 204 are generated to control the synthesis of the Directed Diversity Chemical Library 208 for the next iteration.

Preferably, elements of the present invention are controlled by a data processing device, such as a computer operating in accordance with software. Consequently, it is possible in the present invention to store massive mounts of data, and to utilize this data in a current iteration to generate robotic synthesis instructions 204 for the next iteration. In particular, since the elements of the present invention are controlled by a data processing device, it is possible to store the Structure-Activity Data 210 obtained during each iteration. It is also possible to utilize the historical structure-activity data 212 obtained during previous iterations, as well as other pertinent structure-activity data obtained by other experiments, to generate robotic synthesis instructions 204 for the next iteration. In other words, the synthesis of the Directed Diversity Chemical Library 208 for the next iteration is guided by the results of all previous iterations (or any subset of the previous iterations, as determined by user input, for example). Put another way, the present invention "learns" from its past performance such that the present invention is "intelligent". As a result, the leads 216 identified in subsequent iterations are better (i.e., exhibit physical, chemical and/or biological properties closer to the prescribed values) than the leads 216 identified in prior iterations.

According to a preferred embodiment of the present invention, one or more robots (i.e., the Chemical Synthesis Robot 112) are used to robotically synthesize the Directed Diversity Chemical Library 208 during each iteration. Also, one or more robots (i.e. the analysis robot 116) are used to robotically analyze the compounds contained in the Directed Diversity Chemical Library 208 during each iteration. As used herein, the term "robot" refers to any automated device that automatically performs functions specified by instructions, such as the robotic synthesis instructions 204 which the Chemical Synthesis Robot 112 receives from the Synthesis Protocol Generator 104. The integrated use of data processing devices (i.e., the Synthesis Protocol Generator 104) and robots (i.e., the Chemical Synthesis Robot 112 and the analysis robot 116) in the present invention enables the automatic and intelligent synthesis and screening of very large numbers of chemical compounds.

The structure and operation of the present invention shall now be described in greater detail.

2. Structure of the Present Invention

Figure 1:
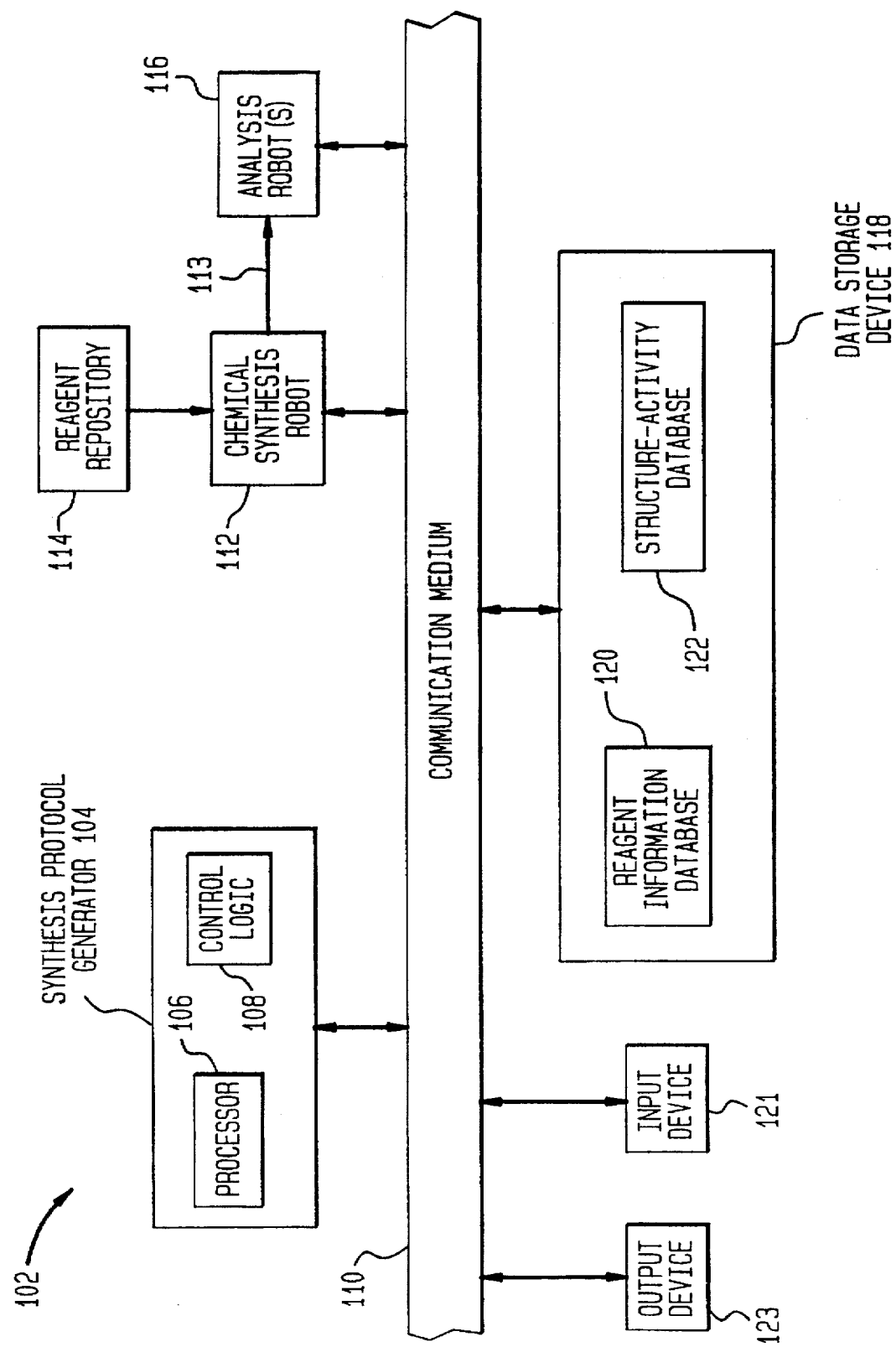
FIG. 1 is a block diagram of a lead generation system according to a preferred embodiment of the present invention.

FIG. 1 is a structural block diagram of a lead generation/optimization system 102 according to a preferred embodiment of the present invention. The drug lead generation system 102 comprises a central processing unit (CPU), such as a processor 106, which operates according to control logic 108. According to the present invention, the processor 106 and the control logic 108 collectively represent a Synthesis Protocol Generator 104.

The control logic 108 preferably represents a computer program such that the processor 106 operates according to software instructions contained in the control logic 108. Alternatively, the processor 106 and/or the control logic 108 are implemented as a hardware state machine.

A suitable form for the processor 106 is an Indigo, Indy, Onyx, Challenge, or Power Challenge computer made by Silicon Graphics, Inc., of Mountain View, Calif. Another suitable form for the processor 106 is a Connection Machine computer made by Thinking Machines Corporation of Boston, Mass. Any other suitable computer system could alternatively be used.

A communication medium 110, comprising one or more data buses and/or IO (input/output) interface devices, connect the Synthesis Protocol Generator 104 to a number of peripheral devices, such as an input device 121, an output device 123, a Chemical Synthesis Robot 112, one or more analysis robots 116, and a data storage device 118.

The input device 121 receives input (such as data, commands, etc.) from human operators and forwards such input to the Synthesis Protocol Generator 104 via the communication medium 110. Any well known, suitable input device may be used in the present invention, such as a keyboard, pointing device (mouse, roller ball, track ball, light pen, etc.), touch screen, etc. User input may also be stored and then retrieved, as appropriate, from data/command files.

The output device 123 outputs information to human operators. The Synthesis Protocol Generator 104 transfers such information to the output device 123 via the communication medium 110. Any well known, suitable output device may be used in the present invention, such as a monitor, a printer, a floppy disk drive, a text-to-speech synthesizer, etc.

The Chemical Synthesis Robot 112 receives robotic synthesis instructions from the Synthesis Protocol Generator 104 via the communication medium 110. The Chemical Synthesis Robot 112 operates according to the robotic synthesis instructions to selectively combine a particular set of reagents from a Reagent Repository 114 to thereby generate structurally and functionally diverse chemical compounds. These chemical compounds form a Directed Diversity Chemical Library 208.

The Chemical Synthesis Robot 112 is preferably capable of mix-and-split, solid phase chemistry for coupling chemical building blocks. The Chemical Synthesis Robot 112 preferably performs selective microscale solid state synthesis of a specific combinatorial library of directed diversity library compounds. The Chemical Synthesis Robot 112 preferably cleaves and separates the compounds of the Directed Diversity Chemical Library 208 (FIG. 2) from support resin and distributes the compounds into preferably 96 wells with from 1 to 20 directed diversity library compounds per well, corresponding to an output of 96 to 1920 compounds per synthetic cycle iteration. This function may alternatively be performed by a well known liquid transfer robot (not shown). Chemical synthesis robots suitable for use with the present invention are well known and are commercially available from a number of manufacturers, such as the following:

TABLE 1

| Manufacturer | City | State | Model |
|---|---|---|---|
| Advanced ChemTech | Louisville | KY | 357 MPS |
|  |  |  | 390 MPS |
| Rainin | Woburn | MA | Symphony |
| Perkin-Elmer Corporation Applied Biosystems Division | Foster City | CA | 433A |
| Millipore | Bedford | MA | 9050 Plus |

All of the instruments listed in Table 1 perform solid support-based peptide synthesis only. The Applied Biosystems and the Millipore instruments are single peptide synthesizers. The Rainin Symphony is a multiple peptide synthesizer capable of producing up to 20 peptides simultaneously. The Advanced ChemTech instruments are also multiple peptide synthesizers, but the 357 MPS has a feature utilizing an automated mix-and-split technology. The peptide synthesis technology is preferred in producing the directed diversity libraries associated with the present invention. See, for example, Gallop, M. A. et al., *J. Med. Chem.* 37, 1233–1250 (1994), which is herein incorporated by reference in its entirety.

Peptide synthesis is by no means the only approach envisioned and intended for use with the present invention. Other chemistries for generating chemical diversity libraries can also be used. For example, the following are suitable: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomeres such as hydantoins, benzodiazepines and dipeptides (Hobbs DeWitt, S. et al., *Proc. Nat. Acad. Sci. USA* 90: 6909–6913 (1993)), vinylogous polypeptides (Hagihara et al., *J. Amer. Chem. Soc.* 114: 6568 (1992)), nonpeptidal peptidomimetics with a Beta-D-Glucose scaffolding (Hirschmann, R. et al., *J. Amer. Chem. Soc.* 114: 9217–9218 (1992)), analogous organic syntheses of small compound libraries (Chen, C. et al., *J. Amer. Chem. Soc.* 116: 2661 (1994)), oligocarbamates (Cho, C. Y. et al., *Science* 261:1303 (1993)), and/or peptidyl phosphonates (Campbell, D. A. et al., *J. Org. Chem.* 59:658 (1994)). See, generally, Gordon, E. M. et al., *J. Med. Chem.* 37:1385 (1994). The contents of all of the aforementioned publications are incorporated herein by reference.

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist.

Any of the above devices are suitable for use with the present invention. The nature and implementation of modifications to these devices (if any) so that they can operate as discussed herein will be apparent to persons skilled in the relevant art.

The analysis robots 116 receive the chemical compounds synthesized by the Chemical Synthesis Robot 112. This is indicated by arrow 113. The analysis robots 116 analyze these compounds to obtain structure-activity data pertaining to the compounds.

Figure 9:
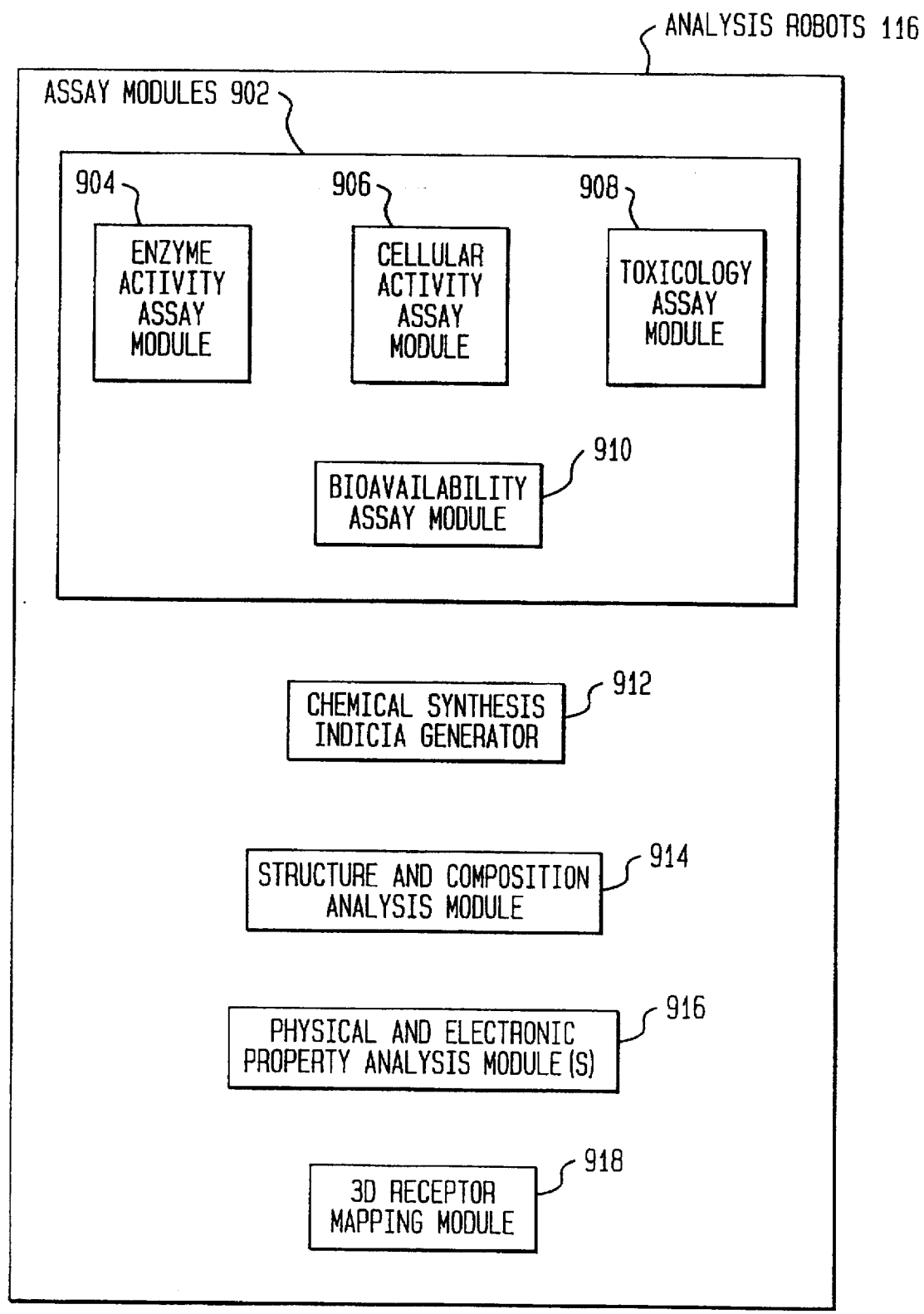
FIG. 9 is a preferred block diagram of analysis robots which are part of the lead generation system of the present invention.

FIG. 9 is a more detailed structural block diagram of the analysis robots 116. The analysis robots 116 include one or more assay modules 902, such as an enzyme activity assay module 904, a cellular activity assay module 906, a toxicology assay module 908, and/or a bioavailability assay module 910. The enzyme activity assay module 904 assays the compounds synthesized by the Chemical Synthesis Robot 112 using well known procedures to obtain enzyme activity data relating to the compounds. The cellular activity assay module 906 assays the compounds using well known procedures to obtain cellular activity data relating to the compounds. The toxicology assay module 908 assays the compounds using well known procedures to obtain toxicology data relating to the compounds. The bioavailability assay module 910 assays the compounds using well known procedures to obtain bioavailability data relating to the compounds.

The enzyme activity assay module 904, cellular activity assay module 906, toxicology assay module 908, and bioavailability assay module 910 are implemented in a well known manner to facilitate the preparation of solutions, initiation of the biological or chemical assay, termination of the assay (optional depending on the type of assay) and measurement of the results, commonly using a counting device, spectrophotometer, fluorometer or radioactivity detection device. Each of these steps can be done manually or by robots in a well known manner. Raw data is collected and stored on magnetic media under computer control or input manually into a computer. Useful measurement parameters such as dissociation constants or 50% inhibition concentrations can then be manually or automatically calculated from the observed data, stored on magnetic media and output to a relational database.

The analysis robots 116 optionally include a structure and composition analysis module 914 to obtain two dimensional structure and composition data relating to the compounds. Preferably, the structure and composition analysis module 914 is implemented using a liquid chromatograph device and/or a mass spectrometer. In one embodiment, a sampling robot (not shown) transfers aliquots from the 96 wells to a coupled liquid chromatography—mass spectrometry system to perform sample analysis.

The structure and composition analysis module 914 may be utilized to determine product composition and to monitor reaction progress by comparison of the experimental results to the theoretical results predicted by the Synthesis Protocol Generator 104. The analysis module may use, but is not limited to, infra-red spectroscopy, decoding of a molecular tag, mass spectrometry (MS), gas chromatography (GC), liquid chromatography (LC), or combinations of these techniques (i.e., GC-MS, LC-MS, or MS-MS). Preferably, the structure and composition analysis module 914 is implemented using a mass spectrometric technique such as Fast Atom Bombardment Mass Spectrometry (FABSMS) or triple quadrapole ion spray mass spectrometry, optionally coupled to a liquid chromatograph, or matrix-assisted laser desorption ionization time-of-flight mass spectrometry (MALDI-TOF MS). MALDI-TOF MS is well known and is described in a number of references, such as: Brummell et al., *Science* 264:399 (1994); Zambias et al., *Tetrahedron Lett.* 35:4283 (1994), both incorporated herein by reference in their entireties.

Liquid chromatograph devices, gas chromatograph devices, and mass spectrometers suitable for use with the present invention are well known and are commercially available from a number of manufacturers, such as the following:

TABLE 2

GAS CHROMATOGRAPHY

| Manufacturer | City | State | Model |
|---|---|---|---|
| Hewlett-Packard Company | Palo Alto | CA | 5890 |
| Varian Associates | Palo Alto | CA | |
| Shimadzu Scientific Inst. | Columbia | MD | GC-17A |
| Fisons Instruments | Beverly | MA | GC 8000 |

TABLE 3

LIQUID CHROMATOGRAPHY

| Manufacturer | City | State | Model |
|---|---|---|---|
| Hewlett-Packard Company | Palo Alto | CA | 1050, 1090 |
| Varian Associates Inc. | Palo Alto | CA | |
| Rainin Instrument Co. | Woburn | MA | |
| Shimadzu Scientific Inst. | Columbia | MD | LC-10A |
| Waters Chromatography | Milford | MA | Millennium |
| Perkin-Elmer Corporation | Norwalk | CT | |
| Hitachi Instruments Inc. | San Jose | CA | |

TABLE 4

MASS SPECTROSCOPY

| Manufacturer | City | State | Model |
| --- | --- | --- | --- |
| Hewlett-Packard Company | Palo Alto | CA | |
| Varian Associates Inc. | Palo Alto | CA | |
| Kratos Analytical Inc. | Ramsey | NJ | MS80RFAQ |
| Finnigan MAT | San Jose | CA | Vision 2000, TSQ-700 |
| Fisons Instruments | Beverly | MA | API LC/MS, AutoSpec |
| Perkin-Elmer Sciex | Norwalk | CT | API-III |

Modifications to these devices may be necessary to fully automate both the loading of samples on the systems as well as the comparison of the experimental and predicted results. The extent of the modification may vary from instrument to instrument. The nature and implementation of such modifications will be apparent to persons skilled in the art.

The analysis robots 116 may optionally further include a chemical synthesis indicia generator 912 which analyzes the structure and composition data obtained by the structure and composition analysis module 914 to determine which compounds were adequately synthesized by the Chemical Synthesis Robot 112, and which compounds were not adequately synthesized by the Chemical Synthesis Robot 112. Preferably, the chemical synthesis indicia generator 912 is implemented using a processor, such as processor 106, operating in accordance with appropriate control logic, such as control logic 108. Preferably, the control logic 108 represents a computer program such that the processor 106 operates in accordance with instructions in the control logic 108 to determine which compounds were adequately synthesized by the Chemical Synthesis Robot 112, and which compounds were not adequately synthesized by the Chemical Synthesis Robot 112. Persons skilled in the relevant art will be able to produce such control logic 108 based on the discussion of the chemical synthesis indicia generator 912 contained herein.

The analysis robots 116 may also include a three dimensional (3D) receptor mapping module 918 to obtain three dimensional structure data relating to a receptor binding site. The 3D receptor mapping module 918 preferably determines the three dimensional structure of a receptor binding site empirically through x-ray crystallography and/or nuclear magnetic resonance spectroscopy, and/or as a result of the application of extensive 3D QSAR (quantitative structure-activity relationship) and receptor field analysis procedures, well known to persons skilled in the art and described in: "Strategies for Indirect Computer-Aided Drug Design", Gilda H. Loew et al., *Pharmaceutical Research*, Volume 10, No. 4, pages 475-486 (1993); "Three Dimensional Structure Activity Relationships", G. R. Marshall et al., *Trends In Pharmceutical Science*, 9:285-289 (1988). Both of these documents are herein incorporated by reference in their entireties.

The analysis robots 116 may additionally include a physical and/or electronic property analysis module(s) 916 which analyzes the compounds synthesized by the Chemical Synthesis Robot 112 to obtain physical and/or electronic property data relating to the compounds. Such properties may include water/octanol partition coefficients, molar refractivity, dipole moment, fluorescence etc. Such properties may either be measured experimentally or computed using methods well known to persons skilled in the art.

Referring again to FIG. 1, the data storage device 118 is a read/write high storage capacity device such as a tape drive unit or a hard disk unit. Data storage devices suitable for use with the present invention are well known and are commercially available from a number of manufacturers, such as the 2 gigabyte Differential System Disk, pan number FTO-SD8-2NC, and the 10 gigabyte DLT tape drive, part number P-W-DLT, both made by Silicon Graphics, Inc., of Mountain View, Calif. A reagent database 120 and a Structure-Activity Database 122 are stored in the data storage device 118.

The reagent database 120 contains information pertaining to the reagents in the Reagent Repository 114. In particular, the reagent database 120 contains information pertaining to the chemical substructures, chemical properties, physical properties, biological properties, and electronic properties of the reagents in the Reagent Repository 114.

The Structure-Activity Database 122 stores Structure-Activity Data 210, 212 (FIG. 2) pertaining to the compounds which were synthesized by the Chemical Synthesis Robot 112. Such Structure-Activity Data 210, 212 is obtained as a result of the analysis of the compounds performed by the analysis robots 116, as described above. The Structure-Activity Data 210, 212 obtained by the analysis robots 116 is transferred to and stored in the Structure-Activity Database 122 via the communication medium 110.

Figure 7:
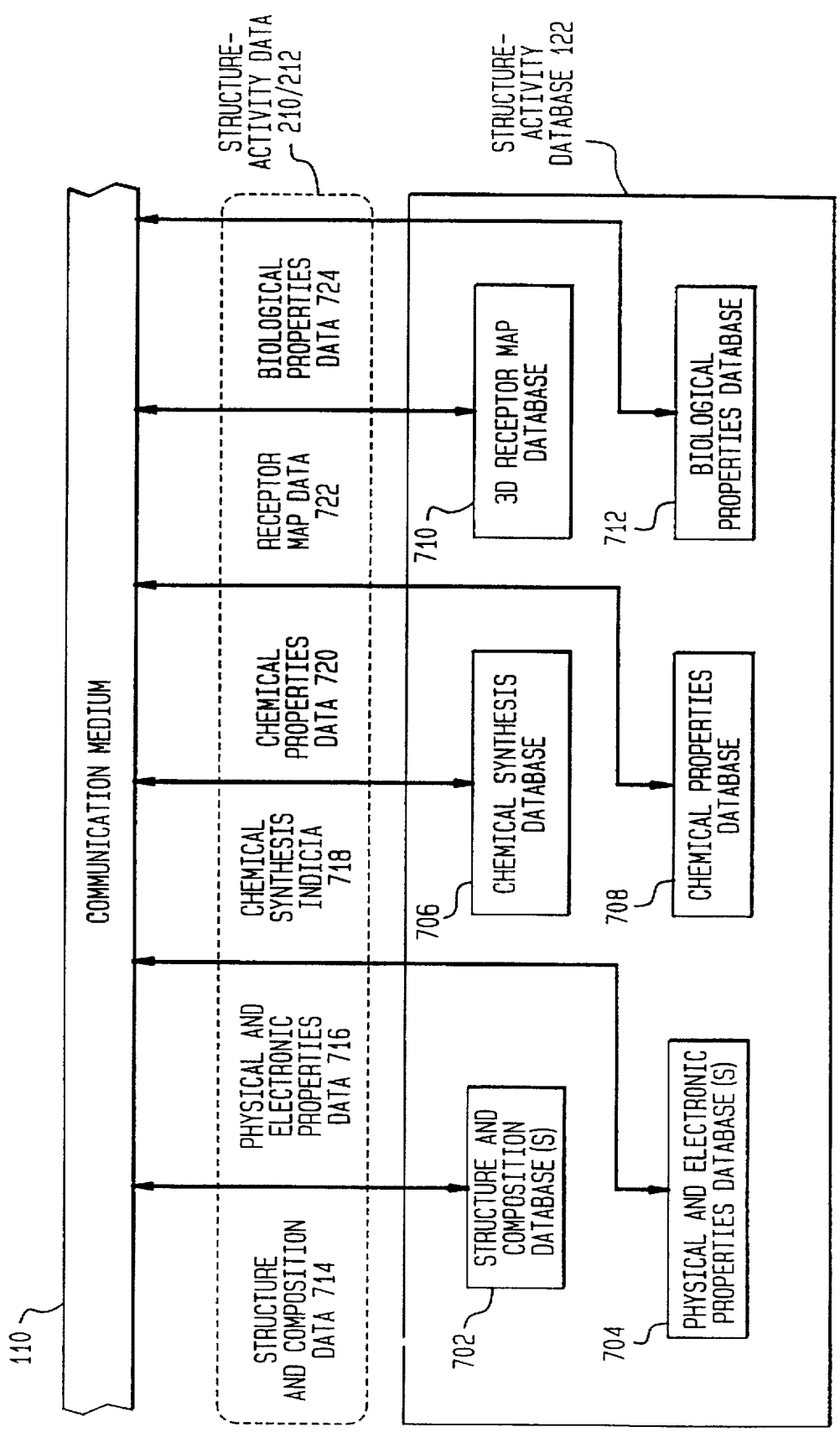
FIG. 7 is a preferred block diagram of a structure-activity database which forms a part of the lead generation system of the present invention.

FIG. 7 is a more detailed block diagram of the Structure-Activity Database 122. The Structure-Activity Database 122 includes a structure and composition database 702, a physical and electronic properties database(s) 704, a chemical synthesis database 706, a chemical properties database 708, a 3D receptor map database 710, and a biological properties database 712. The structure and composition database 702 stores structure and composition data 714 pertaining to compounds synthesized by the Chemical Synthesis Robot 112 and analyzed by the analysis robots 116. Similarly, the physical and electronic properties database 704, chemical synthesis database 706, chemical properties database 708, 3D receptor map database 710, and biological properties database 712 store physical and electronic properties data 716, chemical synthesis indicia 718, chemical properties data 720, 3D receptor map data 722, and biological properties data 724, respectively, pertaining to compounds synthesized by the Chemical Synthesis Robot 112 and analyzed by the analysis robots 116. The structure and composition data 714, electronic properties data 716, chemical synthesis indicia 718, chemical properties data 720, receptor map data 722, and biological properties data 724 collectively represent the Structure-Activity Data 210, 212.

Figure 8:
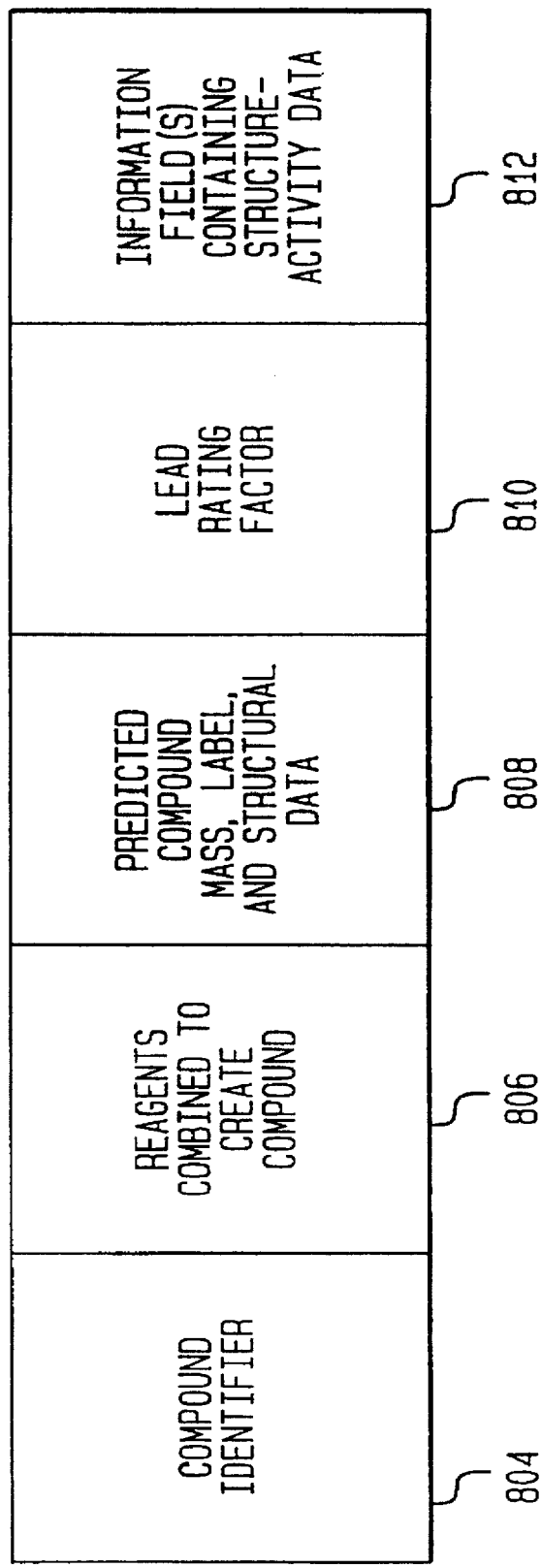
FIG. 8 illustrates a preferred database record format common to records in the structure-activity database.

Preferably, the structure and composition database 702, physical and electronic properties database 704, chemical synthesis database 706, chemical properties database 708, 3D receptor map database 710, and biological properties database 712 each include one record for each chemical compound synthesized by the Chemical Synthesis Robot 112 and analyzed by the analysis robots 116. (Other database structures could alternatively be used.) FIG. 8 depicts a preferred database record format 802 for these records.

Each database record includes: (1) a first field 804 containing information identifying the compound; (2) a second field 806 containing information identifying the reagents from the Reagent Repository 114 that were combined to produce the compound; (3) a third field 808 containing information indicating the predicted mass and structure of the compound and information identifying the label assigned to the compound (the information contained in the third field 808 is described below); (4) a fourth field 810 indicating the rating factor (described below) assigned to the compound; and (5) a fifth field 812 containing structure-activity data. The information stored in the fifth field 812 is database specific (also, the fifth field 812 may include one or more sub-fields). For example, the fifth field 812 in records of the structure and composition database 702 stores structure and composition data 714, whereas the fifth field 812 in records of the electronic properties database 704 stores electronic properties data 716.

3. Operation of the Present Invention

The operation of the lead generation/optimization system 102 shall now be described in detail with reference to a flowchart 302 shown in FIG. 3, and a flow diagram 202 shown in FIG. 2. Flowchart 302 represents the preferred operation of the present invention. The flow diagram 202 depicts the preferred flow of data and materials between the elements of the lead generation system 102.

As stated above, the lead generation/optimization system 102 implements an iterative process where, during each iteration, (1) a Directed Diversity Chemical Library 208 is generated; (2) the compounds in the Directed Diversity Chemical Library 208 are analyzed and new lead compounds 216 are classified, structure-activity/structure-property models with enhanced predictive and discriminating capabilities are constructed, and compounds which are predicted to exhibit improved activity/properties are identified for synthesis during the next iteration; and (3) robotic synthesis instructions 204 are generated to control the synthesis of the Directed Diversity Chemical Library 208 for the next iteration. The steps of flowchart 302 (that is, steps 304–316) are performed during each iteration of this iterative process as indicated by control line 317 in flowchart 302. Generally, (1) the Directed Diversity Chemical Library 208 is generated during step 304; (2) the compounds in the Directed Diversity Chemical Library 208 are analyzed and new lead compounds 216 are classified, structure-activity/structure-property models with enhanced predictive and discriminating capabilities are constructed, and compounds which are predicted to exhibit improved activity/properties are identified for synthesis during the next iteration during steps 306–314; and (3) robotic synthesis instructions 204 are generated to control the synthesis of the Directed Diversity Chemical Library 208 for the next iteration during step 316. The operation of the lead generation/optimization system 102 according to the steps of flowchart 302 shall now be discussed in detail.

Figure 2:
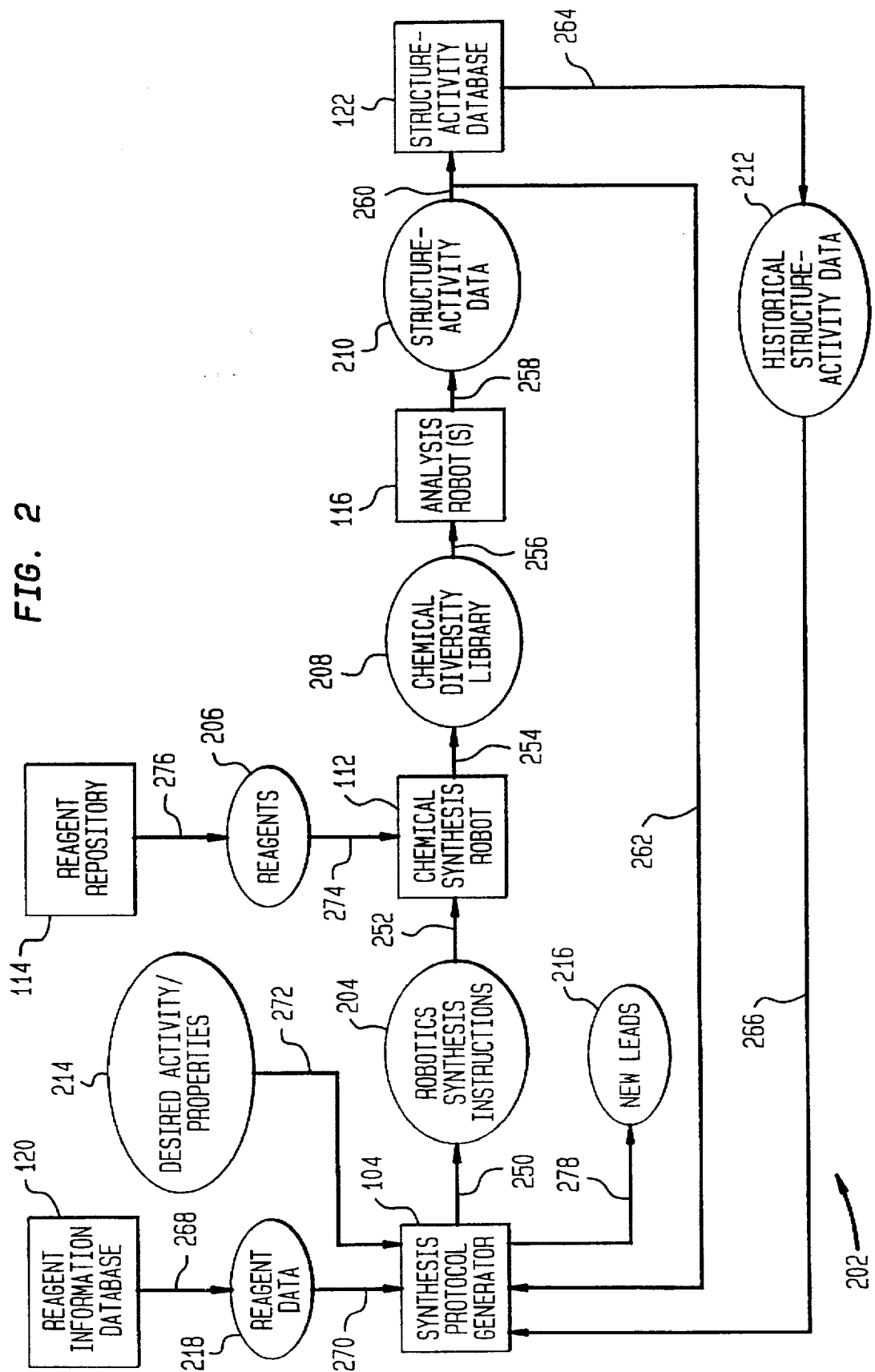
FIG. 2 is a flow diagram depicting the preferred flow of data and materials among elements of the lead generation system of the present invention.
Figure 3:
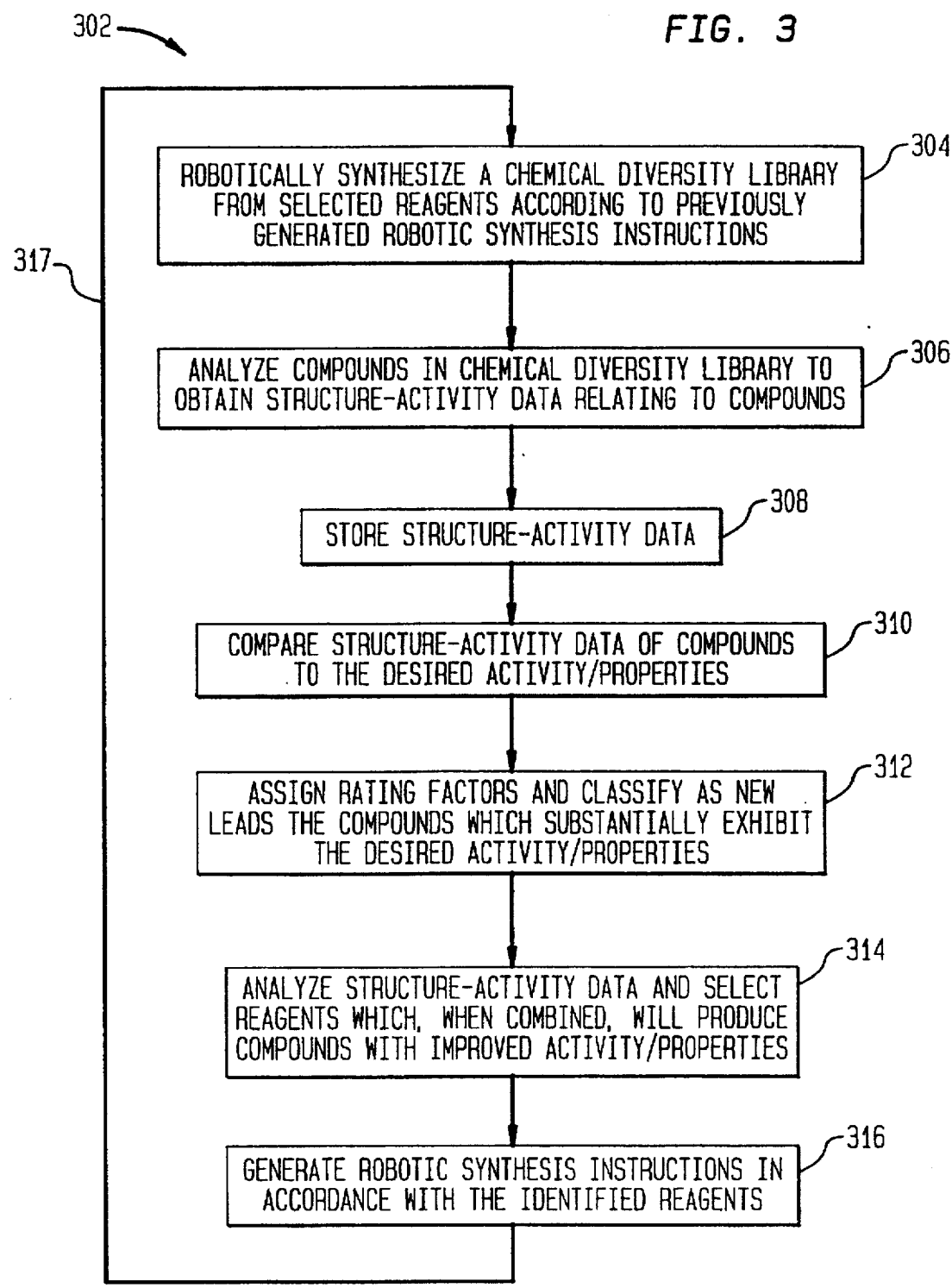
FIGS. 3–6 are flowcharts depicting the operation of the lead generation system according to a preferred embodiment of the present invention.

As represented by step 304, the Chemical Synthesis Robot 112 robotically synthesizes a plurality of chemical compounds in accordance with robotic synthesis instructions 204 (flow arrow 252 in FIG. 2). Preferably, the Chemical Synthesis Robot 112 synthesizes the chemical compounds by selective mixing of reagents 206 from a Reagent Repository 114 (flow arrows 274 and 276 in FIG. 2) in accordance with the robotic synthesis instructions 204. The chemical compounds synthesized by the Chemical Synthesis Robot 112 collectively represent a Directed Diversity Chemical Library 208 (flow arrow 254 in FIG. 2).

The robotic synthesis instructions 204 are generated by a Synthesis Protocol Generator 104 in a manner which is described below (flow arrow 250 in FIG. 2). The robotic synthesis instructions 204 identify which reagents 206 from the Reagent Repository 114 are to be mixed by the Chemical Synthesis Robot 112. The robotic synthesis instructions 204 also identify the manner in which such reagents 206 are to be mixed by the Chemical Synthesis Robot 112 (i.e., which of the reagents 206 are to be mixed together, and under what chemical and/or physical conditions, such as temperature, length of time, stirring, etc.)

As represented by step 306, analysis robots 116 receive the Directed Diversity Chemical Library 208 generated by the Chemical Synthesis Robot 112 (flow arrow 256 in FIG. 2). The analysis robots 116 robotically analyze the chemical compounds in the Directed Diversity Chemical Library 208 to obtain Structure-Activity Data 210 pertaining to such compounds (flow arrow 258 in FIG. 2).

As represented by step 308, the analysis robots 116 store the Structure-Activity Data 210 in a Structure-Activity Database 122 contained in a data storage device 118 (flow arrow 260 in FIG. 2). This structure-activity database 112 also stores structure-activity data pertaining to chemical compounds which were synthesized and analyzed in previous iterations by the Chemical Synthesis Robot 112 and the analysis robots 116, respectively, as well as other pertinent structure-activity data obtained from independent experiments.

The operation of the lead generation/optimization system 102 while performing steps 306 and 308 shall now be discussed in greater detail.

During step 306, assay modules 902 (FIG. 9) robotically assay the chemical compounds in the Directed Diversity Chemical Library 208 to obtain physical properties data 716, chemical properties data 720 and biological properties data 724 (FIG. 7) pertaining to the chemical compounds. For example, the enzyme activity assay module 904 robotically assays the chemical compounds using well known assay techniques to obtain enzyme activity data relating to the compounds. Such enzyme activity data includes inhibition constants $K_i$, maximal velocity $V_{max}$, etc. The cellular activity assay module 906 robotically assays the compounds using well known assay techniques to obtain cellular activity data relating to the compounds. The toxicology assay module 908 robotically assays the compounds using well known assay techniques to obtain toxicology data relating to the compounds. The bioavailability assay module 910 robotically assays the compounds using well know assay techniques to obtain bioavailability data relating to the compounds. Such enzyme activity data, cellular activity data, toxicology data, and bioavailability data represent the physical properties data 716, chemical properties data 720 and the biological properties data 724 shown in FIG. 7. Alternatively, physical properties data 716 may be obtained by the physical and electronic property analysis module 916. In step 308, the physical properties data 716 is stored in the physical properties database 704, the chemical properties data 720 is stored in the chemical properties database 706 and the biological properties data 724 is stored in the biological properties database 712.

Also during step 306, the electronic property analysis module 916 automatically analyzes the chemical compounds contained in the Directed Diversity Chemical Library 208 to obtain electronic properties data 716 pertaining to the chemical compounds. Such electronic properties data 716 is stored in the electronic properties database 704 during step 308.

Additionally during step 306, the 3D receptor mapping module 918 obtains receptor map data 722 representing the three dimensional structure pertaining to a receptor binding site being tested. The 3D receptor mapping module 918 preferably determines the three dimensional structure of the receptor binding site empirically through x-ray crystallography, nuclear magnetic resonance spectroscopy, and/or as result of the application of extensive 3D QSAR and receptor field analysis procedures. Such receptor map data 722 is stored in the 3D receptor map database 710 during step 308.

Also during step 306, an optional structure and composition analysis module 914 analyzes the chemical compounds contained in the Directed Diversity Chemical Library 208 to obtain structure and composition dan 714 pertaining to the chemical compounds. Such structure and composition data 714 is stored in the structure and composition database 702 during step 308.

Figure 4:
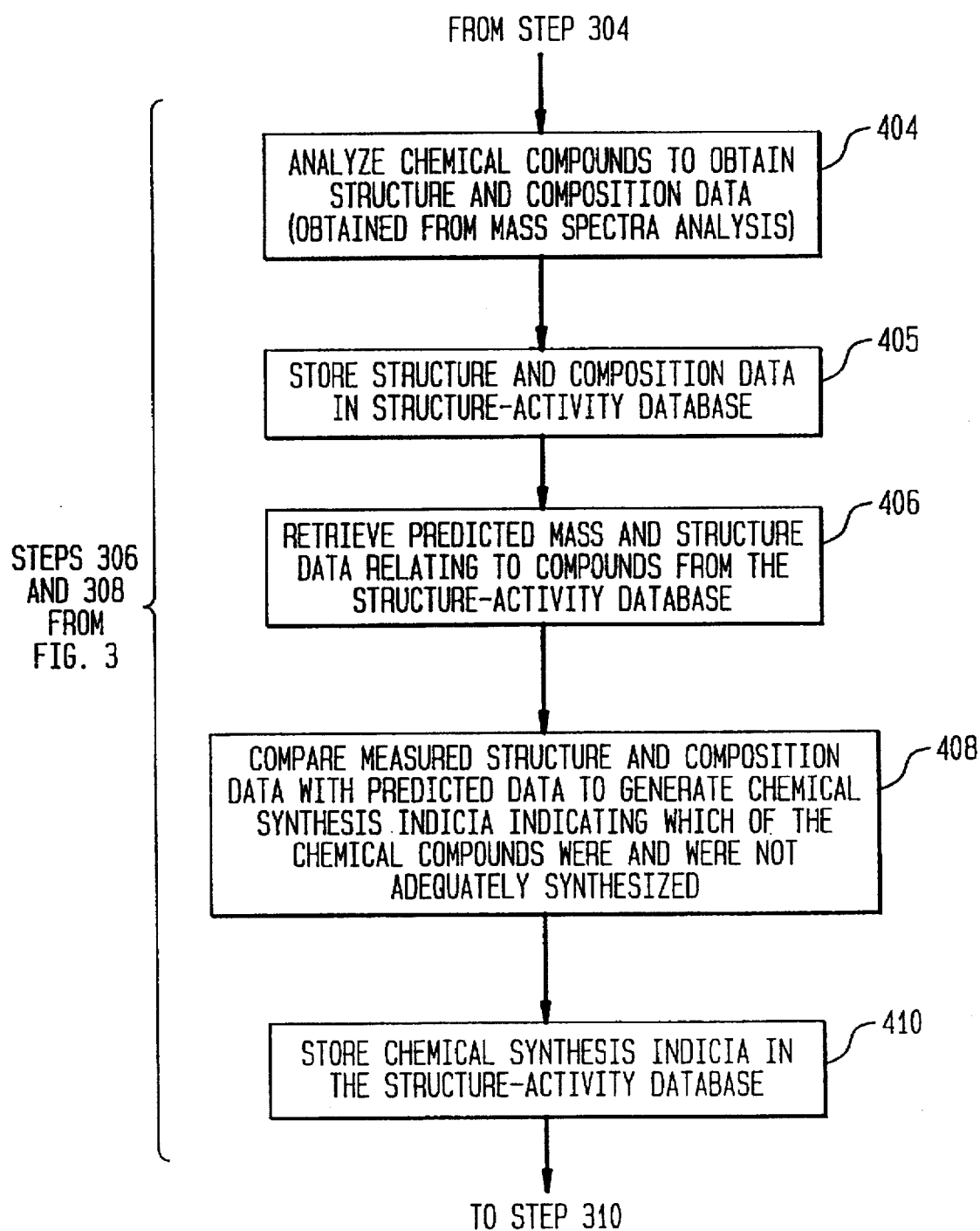

The operation of the structure and composition analysis module 914 (and also the chemical synthesis indicia generator 912) during steps 306 and 308 shall now be further described with reference to a flowchart depicted in FIG. 4.

As represented by step 404, the structure and composition analysis module 914 analyzes the chemical compounds in the Directed Diversity Chemical Library 208 to obtain structure and composition data 714 pertaining to the compounds. Preferably, the structure and composition analysis module 914 analyzes the chemical compounds using well known mass spectra analysis techniques.

As represented by step 405, the structure and composition data 714 is stored in a structure and composition database 702 which forms part of the Structure-Activity Database 122 (FIG. 7).

Figure 5:
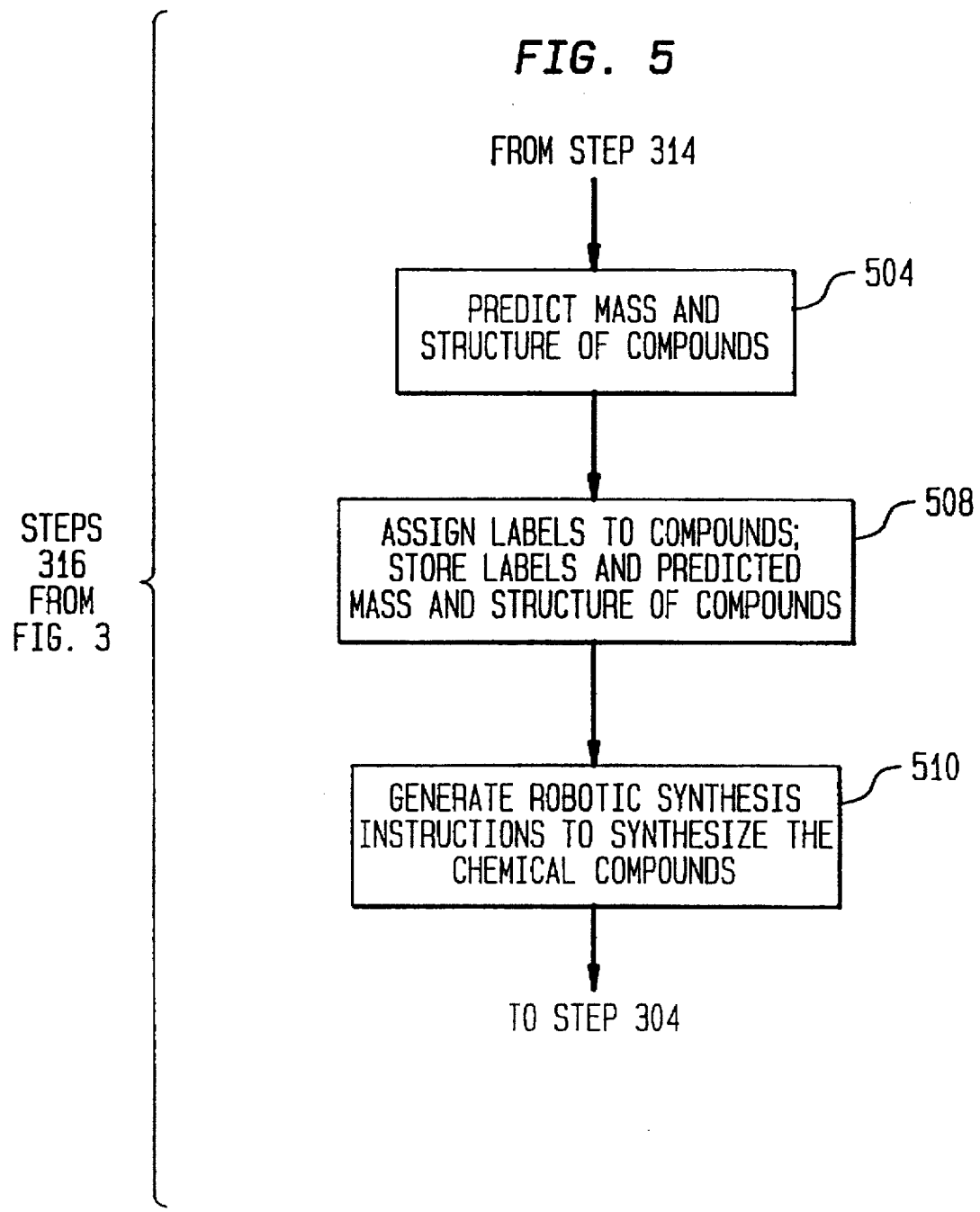

As represented by step 406, the chemical synthesis indicia generator 912 receives the structure and composition data 714. The chemical synthesis indicia generator 912 also retrieves from the Structure-Activity Database 122 the predicted mass and structural data relating to the compounds in the Directed Diversity Chemical Library 208. Such data (i.e., the predicted mass and structural data) is preferably retrieved from the third field 808 (FIG. 8) of the records of the Structure-Activity Database 122 pertaining to the compounds in the Directed Diversity Chemical Library 208. The manner in which the predicted mass and structural data is generated and stored in the Structure-Activity Database 122 is considered in an ensuing discussion pertaining to steps 504 and 508 of FIG. 5.

As represented by step 408, the chemical synthesis indicia generator 912 compares the structure and composition data 714 (obtained by the structure and composition analysis module 914) with the predicted mass and structural data (retrieved from the Structure-Activity Database 122) to generate chemical synthesis indicia 718. The chemical synthesis indicia 718 indicates which of the chemical compounds from the Directed Diversity Chemical Library 208 were adequately synthesized, and which were not adequately synthesized.

Preferably, during step 408 the chemical synthesis indicia generator 912 compares, for each compound, the measured mass of the compound (which is part of the structure and composition data 714) to the predicted mass of the compound. If the measured mass and the predicted mass differ by less than a predetermined mount, then the chemical synthesis indicia generator 912 determines that the chemical compound was adequately synthesized. If the measured mass and the predicted mass differ by more than the predetermined amount, then the chemical synthesis indicia generator 912 determines that the chemical compound was not adequately synthesized. This predetermined amount depends on the sensitivity of the instrument used for the structure and composition analysis.

As represented by step 410, the chemical synthesis indicia generator 912 generates chemical synthesis indicia 718 pertaining to the compounds in the Directed Diversity Chemical Library 208, and stores such chemical synthesis indicia 718 in the chemical synthesis database 706. Such chemical synthesis indicia 718 for each compound is a first value (such as "1") if the compound was adequately synthesized (as determined in step 408), and is a second value (such as "0") if the compound was not adequately synthesized.

The performance of steps 306 and 308 is complete after the completion of step 410. After step 410 is completed, control passes to step 310 (FIG. 3).

As represented by step 310, the Structure-Activity Data 210 pertaining to the compounds in the Directed Diversity Chemical Library 208 is provided to the Synthesis Protocol Generator 104 (flow arrow 262 in FIG. 2). The Synthesis Protocol Generator 104 also receives data pertaining to the desired activity/properties 214 (flow arrow 272 in FIG. 2). This is also called "desired structure/property profile 214" or the "prescribed set". Such data pertaining to desired activity/properties 214 was previously entered by human operators using the input device 121, or read from a file. The Synthesis Protocol Generator 104 compares the Structure-Activity Data 210 of the compounds in the Directed Diversity Chemical Library 208 against the desired activity/properties 214 to determine whether any of the compounds substantially conforms to the desired activity/properties 214.

Preferably, the Synthesis Protocol Generator 104 in step 312 assigns a rating factor to each compound in the Directed Diversity Chemical Library 208, based on how closely the compound's activity/properties match the desired activity/property profile 214. The rating factor may be represented by either numerical or linguistic values. Numerical rating factors represent a sliding scale between a low value (corresponding to an activity/property profile far from the prescribed set 214) and a high value (corresponding to an activity/property profile identical, or very similar, to the prescribed set 214). Linguistic rating factors take values such as "poor," "average," "good," "very good," etc. Preferably, the Synthesis Protocol Generator 104 stores the rating factors of the compounds in the fourth field 810 (FIG. 8) of their respective records in the Structure-Activity Database 122.

Also in step 312, any compound from the Directed Diversity Chemical Library 208 that substantially conforms to the desired activity/properties profile 214 is classified as a new lead compound. The rating factor may also be used to select new leads if an insufficient number of compounds substantially exhibiting the desired activity/properties 214 is found.

As represented by step 314, the Synthesis Protocol Generator 104 retrieves from the Structure-Activity Database 122 historical structure-activity data 212 pertaining to the chemical compounds synthesized in previous iterations (flow arrows 264 and 266). Also during step 314, the Synthesis Protocol Generator 104 accesses the reagent information database 120 and retrieves data 218 pertaining to reagents contained in the Reagent Repository 114 (flow arrows 268 and 270 in FIG. 2). The synthesis protocol generator uses the reagent data 218 and the Structure-Activity Data 210, 212 to identify, under computer control, reagents from the Reagent Repository 114 which, when combined, will produce compounds which are predicted to (1) exhibit improved activity/properties, (2) test the validity of the current structure-activity models, and/or (3) discriminate between the various structure-activity models. Under the system of the present invention, one or more structure-activity models may be tested and evaluated in parallel.

Preferably, during the first iteration of flowchart 302, the Synthesis Protocol Generator 104 uses structural, electronic and physicochemical diversity criteria and, optionally, receptor fit criteria to generate an initial Directed Diversity Chemical Library 208. The initial choice is aimed at maximizing the information content of the resulting chemical library within the domain of interest, as measured by the presence of chemical functionalities, hydrogen bonding characteristics, electronic properties, topological and topographical parameters, etc.

Figure 6:
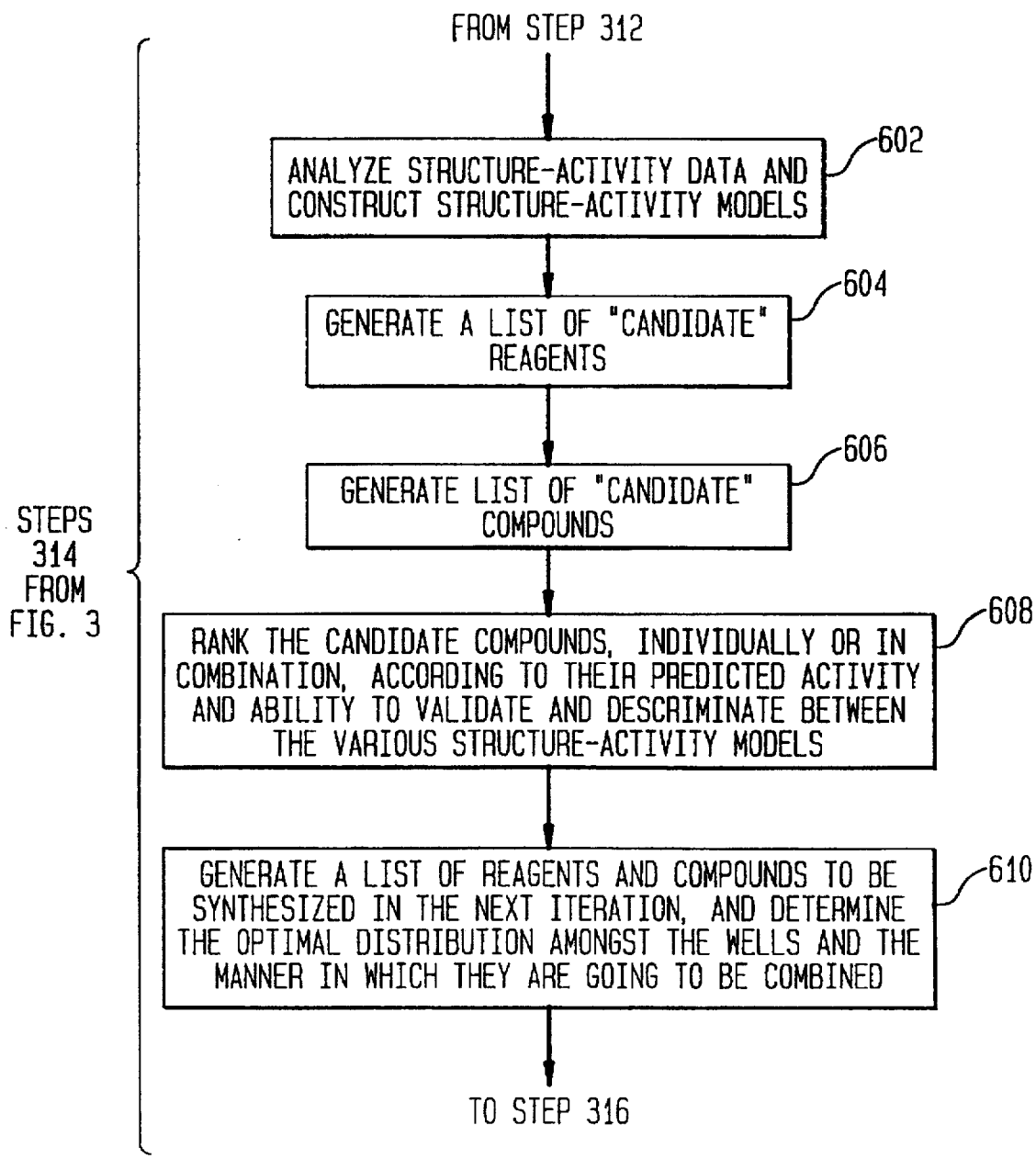

The operation of the Synthesis Protocol Generator 104 while performing step 314 shall now be further described with reference to a flowchart shown in FIG. 6.

As represented by step 602, the Synthesis Protocol Generator 104 analyzes the Structure-Activity Data 210 pertaining to the compounds in the directed diversity library 208 and the historical structure-activity data 212 obtained from previous iterations, and constructs structure-activity models with enhanced predictive and discriminating ability.

In a preferred embodiment of the present invention, step 602 involves the construction of functional structure-activity models, and in particular models wherein the activity is represented as a linear combination of basis functions of one or more molecular features. Such molecular features may include topological indices, physicochemical properties, electrostatic field parameters, volume and surface parameters, etc., and their number may range from a few tens to tens of thousands. The coefficients are preferably determined using linear regression techniques. If many features are used, linear regression may be combined with principal component analysis, which is a well known technique for selecting the most important set of features from a large table.

In a preferred embodiment of the present invention, the basis functions used in the linear regression procedure are selected using a well known genetic function approximation (GFA) algorithm as described in Rogers and Hopfinger, *J. Chem. Inf. Comput. Sci.* 34:854 (1994), which is herein incorporated by reference in its entirety. In the GFA algorithm, a structure-activity model is represented as a linear string which encodes the features and basis functions employed by the model. A population of linearly encoded structure-activity models is then initialized by a random process, and allowed to evolve through the repeated application of genetic operators, such as crossover, mutation and selection. Selection is based on the relative fitness of the models, as measured by a least squares error procedure, for example. Friedman's lack-of-fit algorithm, described in J. Friedman, Technical Report No. 102, Laboratory for Computational Statistics, Department of Statistics, Stanford University, Stanford, Calif., November 1988, herein incorporated by reference in its entirety, or other suitable metrics well known to persons skilled in the art, may also be used. GFA can build models using linear polynomials as well as higher-order polynomials, splines and Gaussians. Upon completion, the procedure yields a population of models, ranked according to their fitness score.

The present invention employs a plurality of analytic filters (represented by steps 604 and 606) to intelligently select reagents (from the Reagent Repository 114) to use during the next iteration, and to more intelligently select compounds to synthesize during the next iteration. The use of such analytic filters increases the probability that the compounds ultimately selected for synthesis during the next iteration will exhibit improved activity/properties. Since the method only synthesizes and analyzes compounds which have a high probability of having the desired activity/ properties 214, the present invention is much more efficient, effective, and expedient than conventional lead generation processes.

As represented by step 604, the Synthesis Protocol Generator 104 applies a first sequence of analytic filters to identify candidate reagents from the Reagent Repository 114 which are appropriate for the generation of the directed diversity chemical library for the next iteration. Such filters may identify and select reagents based on a number of factors, including (but not limited to) the cost of the reagents, the presence or absence of certain functional groups and/or hydrogen bonding characteristics, conformational flexibility, predicted receptor fit, etc.

As represented by step 606, the Synthesis Protocol Generator 104 generates a list of compounds based on the reagents selected in step 604. Each of these compounds incorporates one or more of the reagents identified in step 604. In one embodiment of the invention, the Synthesis Protocol Generator 104 generates the list of compounds by combining these reagents in every possible way for a given compound length, such as three (in which case the compounds in the list would be trimers).

Not all of these compounds in the list will be synthesized during the next iteration. The Synthesis Protocol Generator 104 in step 606 applies a second sequence of analytic filters to identify candidate compounds from the list of compounds which are appropriate for the generation of the Directed Diversity Chemical Library 208 for the next iteration. These analytic filters base their analysis on a number of factors, including (but not limited to) total volume and surface area, conformational flexibility, receptor complementarity, etc. These analytic filters may also base their analysis on whether a compound was previously successfully or unsuccessfully synthesized (as indicated by the chemical synthesis indicia 718, described above). According to an embodiment of the present invention, the candidate compounds identified by operation of the first and second sequences of filters are synthesized during the next iteration to generate a new Directed Diversity Chemical Library 208.

According to an alternate embodiment of the present invention, the primary use of the first and second sequence of filters, particularly the filters employed in step 606, is to eliminate unsuitable compounds from further consideration, rather than to select a set of compounds to synthesize for the next iteration. In this alternate embodiment, the selection of a set of compounds to synthesize for the next iteration is performed in step 608. The set of compounds determined in step 608 is an optimal or near-optimal one.

As represented by step 608, the Synthesis Protocol Generator 104 ranks the candidate compounds identified in step 606, individually or in combination, according to their predicted ability to (1) exhibit improved activity/properties, (2) test the validity of the current structure-activity models, and/or (3) discriminate between the various structure-activity models. The candidate compounds may also be ranked according to their predicted three-dimensional receptor fit. The phrase "individually or in combination" means that the Synthesis Protocol Generator 104 analyzes and ranks the candidate compounds each standing alone, or, alternatively, analyzes and ranks sets of the candidate compounds.

In a preferred embodiment of the present invention, the highest-ranking models identified in step 602 are used in step 608 to select a set of compounds which, as a set, best satisfy the following requirements: (1) exhibit improved activity as predicted by the highest ranking structure-activity models, (2) test the validity of the highest ranking structure-activity models, and/or (3) discriminate between the highest ranking structure-activity models. Requirements (2) and (3) allow for the selection of compounds which need not necessarily exhibit improved activity but, rather, prove or disprove some of the highest ranking structure-activity models, or discriminate most effectively between them. In other words, requirements (2) and (3) enable the elaboration or improvement of the models from one iteration to the next.

The final set of compounds may contain compounds which satisfy one, two or all three of the conditions listed above. Which requirement is emphasized in any iteration depends on the amount and quality of structure-activity data, the predictive power of the current structure-activity models, and how closely the activity/properties of the compounds in the last directed diversity chemical library match the desired activity/properties. Typically, as more and more directed diversity chemical libraries are generated, emphasis will shift from requirements (2) and (3) to requirement (1).

The task in step 608 of selecting the optimal set of compounds for the next directed diversity chemical library involves a search over the entire set of subsets of the candidate compounds (identified during step 606), wherein each subset has k members, where k may vary from one subset to the next and is preferably within the following range: $1000 \leq k \leq 5000$. Given a list of n compounds produced during step 606, the present invention in step 608 identifies which subset of k compounds best satisfies requirements (1), (2) and (3) outlined above. The number of distinct k-subsets of an n-set S is given by EQ. 1:

$$N = \sum_{k=k_1}^{k_2} \frac{n!}{k!(n-k)!} \quad \text{EQ. 1}$$

where $k_1$ and $k_2$ represent the minimum and maximum number of members in a subset, respectively. As indicated above, $k_1$ is preferably equal to 1000 and $k_2$ is preferably equal to 5000. This task is combinatorially explosive, i.e., in all but the simplest cases, N is far too large to allow for the construction and evaluation of each individual subset given current data processing technology. As a result, a variety of stochastic modeling techniques can be employed, which are capable of providing good approximate solutions to combinatorial problems in realistic time frames. However, the present invention envisions and includes the construction and evaluation of each individual subset once computer technology advances to an appropriate point.

In a preferred embodiment of the present invention, in step 608 each subset of candidate compounds is represented as a binary string which uniquely encode; the number and indices of the candidate compounds comprising the subset. A population of binary encoded subsets is then initialized by a random process, and allowed to evolve through the repeated application of genetic operators, such as crossover, mutation and selection. Selection is based on the relative fitness of the subsets, as measured by their ability to satisfy requirements (1), (2) and (3) discussed above. Upon completion, the present invention yields a population of subsets, ranked according to their ability to satisfy requirements (1), (2) and (3). The highest ranking set is then processed in accordance with step 610.

Figure 10:
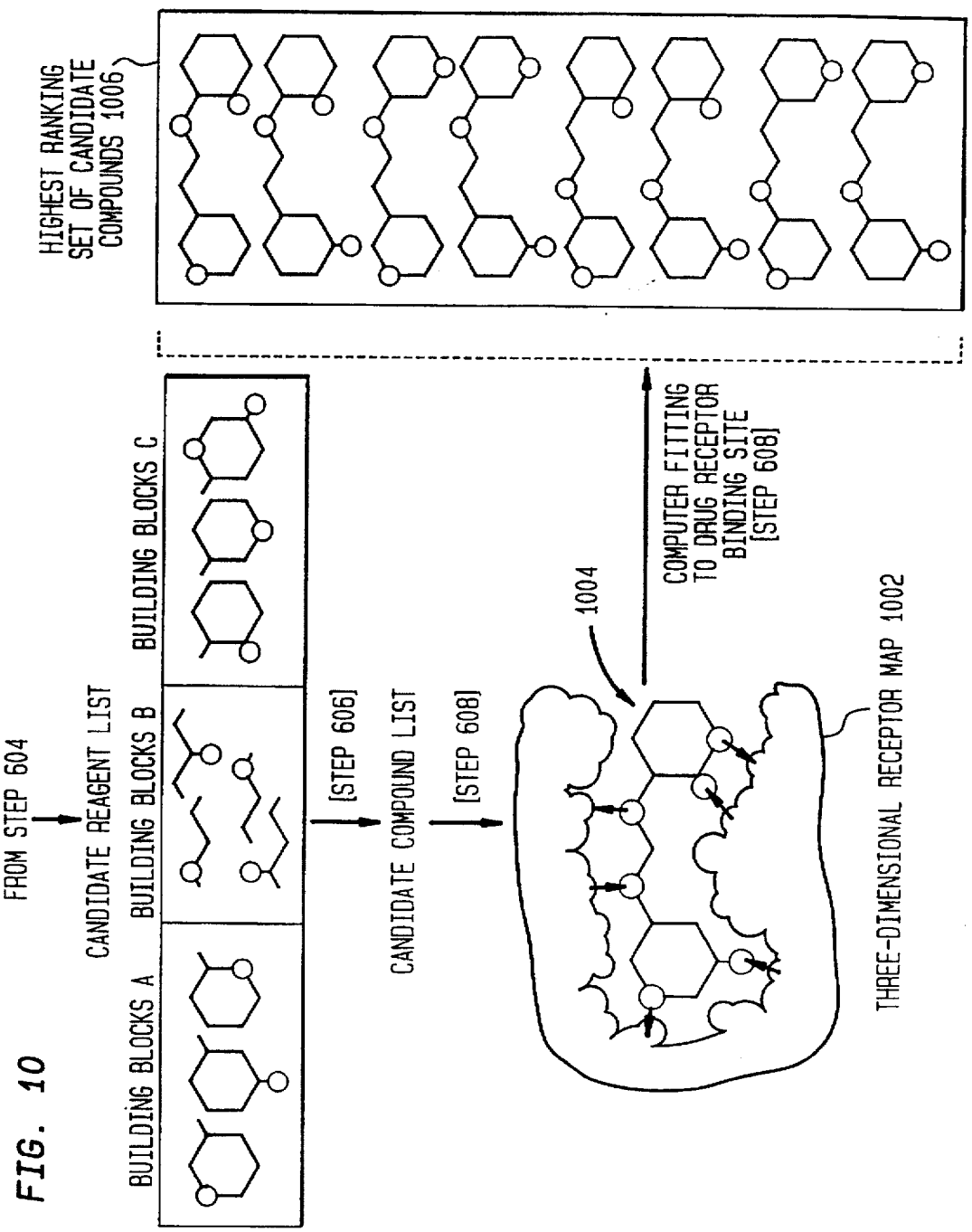
FIG. 10 illustrates an embodiment of the present invention in which candidate compounds are ranked according to their predicted three-dimensional receptor fit.

In a preferred embodiment of the present invention, candidate compounds may also be ranked according to their predicted three-dimensional receptor fit. This is conceptually illustrated in FIG. 10, wherein candidate trimer compounds are generated in step 606 from available building blocks (reagents) A, B, and C (identified in step 604), to produce a list of candidate compounds. These candidate compounds are then evaluated and ranked in step 608 based on their three-dimensional receptor complementarity as well as other criteria (as described herein). FIG. 10 depicts, for illustrative purposes, an example candidate compound 1004 interacting with a three-dimensional receptor map 1002. The highest ranking set 1006 is then processed in accordance with step 610.

As represented by step 610, based on the rankings determined in step 608, the Synthesis Protocol Generator 104 generates a list of compounds to be synthesized during the next iteration, and a list of reagents which, when combined, will produce these compounds, and the manner in which these reagents are to be combined. The Synthesis Protocol Generator 104 also generates a description of how the compounds are to be distributed amongst the individual wells of the Directed Diversity Chemical Library 208. Upon the creation of this data, step 314 is complete, and control passes to step 316 (FIG. 3).

Referring again to FIG. 3, in step 316 the Synthesis Protocol Generator 104 generates robotic synthesis instructions 204 (flow arrow 250 in FIG. 2) which, when executed by the Chemical Synthesis Robot 112, enable the Chemical Synthesis Robot 112 to robotically synthesize (during step 304 of the next iteration of flowchart 302) the chemical compounds from selected combinations of particular reagents 206 from the Reagent Repository 114, as specified in step 314. Such chemical compounds collectively represent a new Directed Diversity Chemical Library 208. The operation of the Synthesis Protocol Generator 104 while performing step 316 shall now be described with reference to a flowchart shown in FIG. 5.

As represented by step 504, the Synthesis Protocol Generator 104 predicts the molecular mass and structure of the compounds identified in step 314 using well known procedures.

As represented by step 508, the Synthesis Protocol Generator 104 assigns a unique label to each of the compounds. Preferably, compounds are stored in 96 well plates, and each unique label is associated with a code that references the wells and plates in which the compound is stored. The purpose of these labels is to track the synthesis, analysis and storage of each individual compound and its associated data. The Synthesis Protocol Generator 104 creates a record in the Structure-Activity Database 122 for each compound. In practice, for each compound, the Synthesis Protocol Generator 104 creates a record in each database of the Structure-Activity Database 122 (see FIG. 7). These records preferably have the format shown in FIG. 8. The Synthesis Protocol Generator 104 stores the labels and the predicted mass and structure information (determined in step 504) associated with the compounds in the third field 808 of these new records.

In step 510, the Synthesis Protocol Generator 104 generates robotic synthesis instructions 204 to synthesize the chemical compounds identified in step 314. The manner in which the Synthesis Protocol Generator 104 generates such robotic synthesis instructions 204 is implementation dependent and is contingent on the particular characteristics of the chemical synthesis robot which is used in the lead generation system 102. The manner in which the Synthesis Protocol Generator 104 generates the robotic synthesis instructions 204 will be apparent to persons skilled in the relevant art.

The performance of step 316 is complete after the completion of step 510. Then, control passes to step 304 (FIG. 3) to begin the next iteration of flowchart 302.

In summary, the present invention is a system and method for automatically generating chemical compounds having desired properties. It should be noted that the terms and phrases "automatically" and "computer controlled" (and the like) as used herein mean that the present invention is capable of operating without human intervention. This is achieved by using automated devices, such as computers and robots. However, it should be understood that the present invention allows and envisions human intervention (i.e., operator aid, operator input, and/or operator control), particularly when selecting compounds for synthesis during the next iteration, and when generating robotic synthesis instructions. Thus, the phrase "computer control" does not rule out the possibility that optional human intervention may be involved in the process. For example, the robotic synthesis instructions may be generated manually in accordance with well known procedures using information provided by the Synthesis Protocol Generator 104. Such human intervention is allowed but optional; the present invention can operate without any human intervention.

In an alternative embodiment of the present invention, a plurality of systems 102 operate in parallel to generate and analyze lead compounds. This is called distributed directed diversity. The systems 102 are preferably centrally controlled by a master computer system (not shown). Details of this master computer system will be apparent to persons skilled in the relevant art.

EXAMPLE

Generation of Lead Thrombin Inhibitor

One example of the present invention is directed towards the generation and analysis of libraries of thrombin inhibitors. This example shall now be discussed.

Thrombin is a serine protease involved in both the blood coagulation cascade and platelet activation. When the circulatory system is injured, a cascade of reactions is initiated which leads to the production of thrombin. Thrombin catalyzes the conversion of fibrinogen to fibrin, which forms polymers, and the activation of factor XIII, which catalyzes fibrin crosslinking leading to the formation of fibrin clots. Thrombin also activates the thrombin receptor, which together with other signals induces platelet aggregation, adhesion and activation, and the formation of haemostatic plugs. Aberrant activation or regulation of the coagulation cascade is a major cause of morbidity and mortality in numerous diseases of the cardiovascular system and their associated surgical treatment. Current medical opinion holds that a triad of treatment regimes, including thrombolytic, antiplatelet and anticoagulant therapy, should be used in a variety of cardiac diseases, including recurrent acute myocardial infarction, peripheral arterial disease, atrial fibrillation and the prevention of thromboembolic complications during valvular replacement, orthopedic surgery and percutaneous angioplasty. There is also an unmet therapeutic need for orally active anticoagulants in deep vein thrombosis. Since thrombin catalyzes the terminal step in the clotting cascade, and also plays a major role in platelet activation, thrombin inhibitors should prove therapeutically effective as anticoagulants, and should additionally possess antiplatelet activity.

In the example being considered herein, the desired bioactivity property is potent inhibition of the thrombin enzyme which is involved in blood clotting. Competitive inhibition of thrombin would prevent both the coagulation and platelet activation processes mediated by thrombin. However, many other proteases in blood and other tissues have specificity profiles similar to thrombin. In particular, plasmin and tissue plasminogen activator, which promote the hydrolysis of fibrin clots and thus have functions crucial to the elimination of circulatory system occlusions, are proteases with primary specificities similar to thrombin. It is also desirable that therapeutically useful thrombin inhibitors do not inhibit these proteases or other enzymes involved in fibrinolysis. Therefore, the properties which are to be optimized include potent thrombin inhibition, but weak or no inhibition of enzymes such as plasmin, tissue plasminogen activator and urokinase.

Each thrombin inhibitor generated by the present invention preferably comprises three sites of variable structure. The use of thrombin inhibitors having three sites is based on the goal, in medicinal drug research, of obtaining a great deal of diversity (both functional and structural) while minimizing molecular space and weight. Trimers are preferably used since, generally, trimers are smaller and lighter than compounds comprising greater numbers of units, such as tetrameric compounds and pentameric compounds. Obtaining drugs with minimum size and molecular weight is an advantage because it generally minimizes cost and maximizes oral bioavailability.

Figure 12:
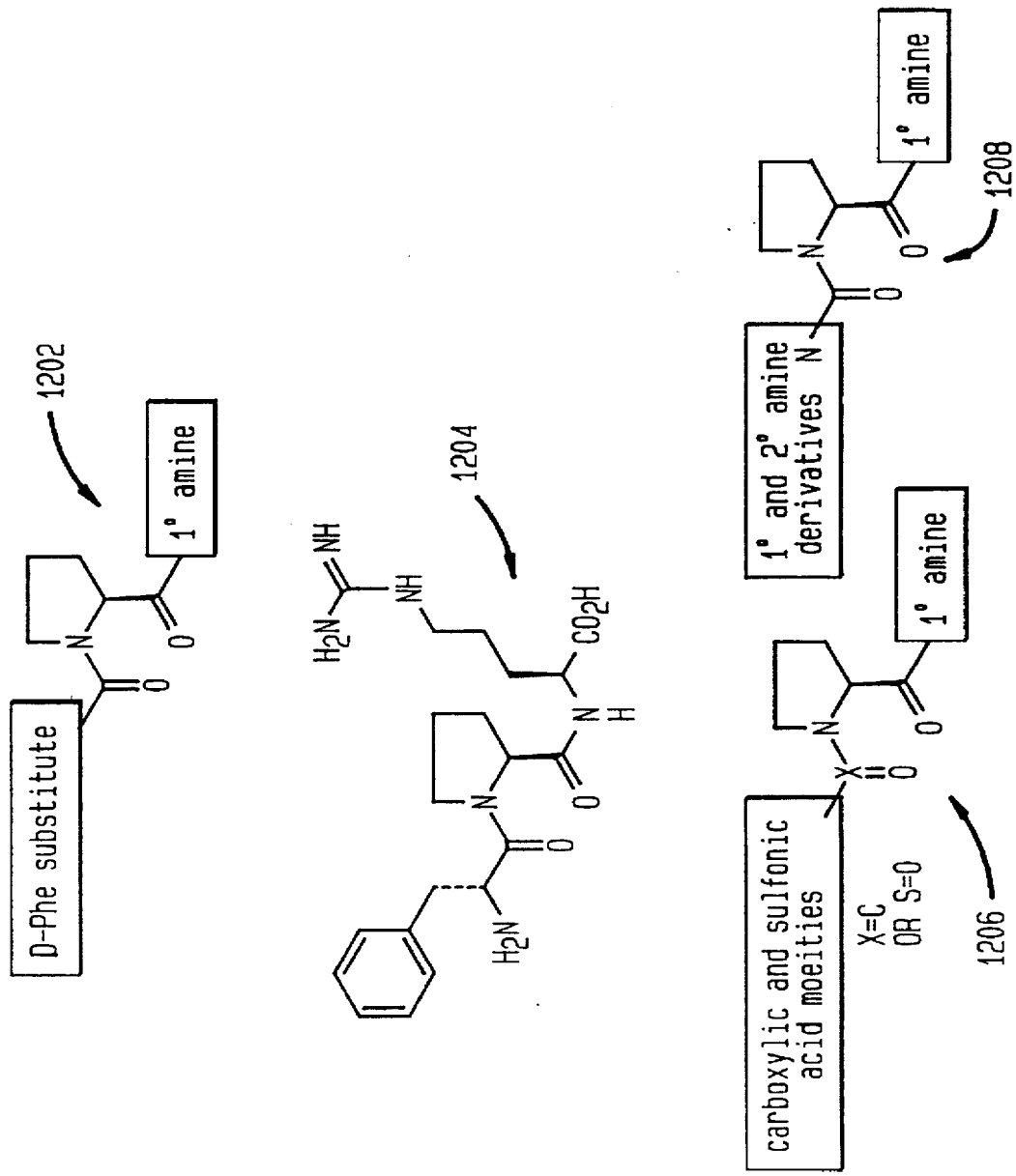
FIG. 12 is a schematic of an example thrombin directed diversity chemical library.

The present example (shown in FIG. 12) is directed towards the generation and analysis of libraries of thrombin inhibitors of type 1202 related to D-Phe-Pro-Arg 1204, wherein the initial directed diversity library is composed of Y-proline-Z, where Y may be one of ten D-Phe substitutes and Z one of 100–500 commercially available primary amines from a Reagent Repository 114. The choice of amines Z and D-Phe substitutes Y is determined under computer control using the Synthesis Protocol Generator 104. The D-Phe substitutes may be derived from any carboxylic acid or sulfonic acid for compounds of type 1206 or, separately, may be a primary or secondary amine linked to the peptide backbone as a urea for compounds of type 1208. Preferably, the directed diversity library 208 for compounds of type 1206 is assembled by the Chemical Synthesis Robot 112 using well known solid phase methods and is released as mixtures of 10 compounds per well in a 96 well format in accordance with the robotic synthesis instructions 204 received from the Synthesis Protocol Generator 104. The initial directed diversity library 208 is assembled using one amine Z and ten D-Phe variants Y per well. More than one 96 well plate may be used, and the resulting directed diversity library 208 may contain 1000–5000 members. The library 208 is then submitted to the analysis robot 116, which analyses the library 208 and generates data pertaining thereto that can be used to evaluate the degree of inhibition of thrombin and other enzymes of interest (such data is called Structure-Activity Data 210).

Based on criteria set forth in the desired activity/property profile 214 (FIG. 2) and the SAR data 210 obtained from the initial directed diversity library, the second iteration directed diversity library is generated using the ten best amines Z. The second iteration directed diversity library 208 is synthesized using solid phase methods and is released as one compound per well in a 96 well format in accordance with the robotic synthesis instructions 204 received from the Synthesis Protocol Generator 104. The directed diversity library 208 is generated from the ten selected amines Z (one amine per well) using D-Phe and D-Phe substitutes Y producing one D-Phe or D-Phe variant per well. This directed diversity library 208 thus contains 100 members. The library 208 is then submitted to the analysis robot 116, to evaluate the degree of inhibition of thrombin and other enzymes of interest (as represented by SAR data 210). This establishes the most active members of the directed diversity library 208 as defined by the criteria set forth in the desired property profile 214.

A third iteration directed diversity library is then assembled based on SAR data 210 obtained from the second iteration library as defined by the criteria set forth in the desired property profile 214 using the ten best amines Z and additional 100–500 D-Phe substitutes Y chosen under computer control. The D-Phe substitute Y may be derived from carboxylic acids or sulfonic acids. The directed diversity library 208 is assembled using well known solid phase methods and released as mixtures of ten compounds per well in a 96 well format according to the robotic synthesis instructions 204 received from the Synthesis Protocol Generator 104. Thus, the third iteration directed diversity library 208 is assembled from ten amines and 100–500 D-Phe substitutes in a manner analogous to the first iteration directed diversity library to produce a 1000–5000 member library. The third iteration library 208 is then submitted to the analysis robot 116, to evaluate the degree of inhibition of thrombin and other enzymes of interest (as represented by SAR data 210).

Based on criteria set forth in the desired property profile 214 and SAR data 210 obtained from the third iteration directed diversity library, the fourth iteration directed diversity library is then generated from the 10 most active mixtures in the third iteration directed diversity library. The fourth iteration directed diversity library 208 is synthesized using solid phase methods analogous to the first iteration directed diversity library and is released as one compound per well in a 96 well format according to the robotic synthesis instructions 204 received from the Synthesis Protocol Generator 104. The fourth iteration directed diversity library 208 is generated from the ten selected D-Phe variants using the ten amines Z from the third iteration directed diversity library. The fourth iteration library 208 is then submitted to the analysis robot 116, to evaluate the degree of inhibition of thrombin and other enzymes of interest (as represented by SAR data 210). This fourth iteration directed diversity library 208 thus contains 100 members and establishes the most active members of the library 208 as defined by the criteria set forth in the desired property profile 214.

This process may be repeated any number of times (as specified by user input, for example) under computer control.

Additionally, this iterative process is repeated for compounds 1208. The new iterations of directed diversity libraries 208 are related to D-Phe substitutes wherein primary or secondary amines are linked to the peptide backbone as a urea moiety. Four generations of directed diversity libraries are performed as above with these new D-Phe substitutes to produce a new chemically distinct series of chemical leads.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A system for generating compounds having a prescribed set of activity/properties, comprising:

chemical synthesis means for synthesizing, in accordance with synthesis instructions, a directed diversity chemical library comprising a plurality of chemical compounds;

analysis means for analyzing said chemical compounds to obtain structure-activity data pertaining thereto;

comparing means for comparing said structure-activity data of said chemical compounds against said prescribed set of activity/properties to identify any of said chemical compounds substantially conforming to said prescribed set of activity/properties;

classifying means for classifying said identified chemical compounds as lead compounds;

structure-activity model derivation means for analyzing said structure-activity data of said compounds and historical structure-activity data pertaining to compounds synthesized and analyzed in the past to derive structure-activity models having enhanced predictive and discriminating capabilities;

reagent identifying means for identifying, in accordance with said structure-activity models, reagents from a reagent database that, when combined, will produce a set of compounds predicted to exhibit activity/properties more closely matching said prescribed set of activity/properties; and synthesis instruction generating means for generating synthesis instructions that, when executed, enable said chemical synthesis means to synthesize said set of compounds.

2. The system of claim 1, wherein said analysis means comprises at least one of an assay module, a chemical synthesis indicia generator, a structure and composition analysis module, a physical and electronic property analysis module, and a three dimensional receptor mapping module.

3. A computer assisted method for at least partially automatically generating compounds having a prescribed set of properties, comprising the steps of:

(1) synthesizing, in accordance with synthesis instructions, a directed diversity chemical library comprising a plurality of chemical compounds;

(2) analyzing said chemical compounds to obtain structure-activity data pertaining thereto;

(3) comparing, under the assistance of a computer, said structure-activity data of said chemical compounds against said prescribed set of properties to identify any of said chemical compounds substantially conforming to said prescribed set of properties;

(4) classifying said identified chemical compounds as lead compounds;

(5) analyzing, under the assistance of a computer, said structure-activity data of said compounds and historical structure-activity data pertaining to compounds synthesized and analyzed in the past to derive structure-activity models having enhanced predictive and discriminating capabilities;

(6) identifying, in accordance with said structure-activity models, reagents from a reagent database that, when combined, will produce a set of compounds predicted to exhibit activity/properties more closely matching said prescribed set of properties;

(7) generating synthesis instructions that, when executed, enable synthesis of said set of compounds; and (8) repeating steps (1)–(7), wherein step (1) is repeated using said generated synthesis instructions.

4. The method of claim 3, wherein step (6) comprises the step of:

identifying reagents from a reagent database that, when combined, will produce a second set of compounds predicted to have a superior ability to validate said structure-activity models, wherein said first and second sets of compounds are not mutually exclusive;

wherein step (7) comprises the step of generating synthesis instructions that, when executed, enable synthesis of said second set of compounds.

5. The method of claim 3, wherein step (6) comprises the step of:

identifying reagents from a reagent database that, when combined, will produce a second set of compounds predicted to have a superior ability to discriminate between said structure-activity models, wherein said first and second sets of compounds are not mutually exclusive;

wherein step (7) comprises the step of generating synthesis instructions that, when executed, enable synthesis of said second set of compounds.

6. The method of claim 3, wherein step (6) comprises the step of:

identifying reagents from a reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;

wherein step (7) comprises the step of generating synthesis instructions that, when executed, enable synthesis of said second and third set of compounds.

7. The method of claim 3, wherein step (6) comprises the step of:

identifying reagents from a reagent database that, when combined, will produce a second set of compounds predicted to have superior three-dimensional receptor fit, wherein said first and second sets of compounds are not mutually exclusive;

wherein step (7) comprises the step of generating synthesis instructions that, when executed, enable synthesis of said second set of compounds.

8. The method of claim 3, wherein step (6) is performed according to operator input.

9. The method of claim 3, wherein step (7) comprises the steps of:

receiving operator input pertaining to the generation of said synthesis instructions; and generating said synthesis instructions based, at least in part, on said operator input.

10. A synthesis protocol generator for use in a system that endeavors to generate compounds having a prescribed set of activity/properties, said synthesis protocol generator comprising:

structure-activity model derivation means for analyzing structure-activity data of compounds contained in a directed diversity chemical library and historical structure-activity data pertaining to compounds synthesized and analyzed in the past to derive structure-activity models having enhanced predictive and discriminating capabilities;

reagent identifying means for identifying, in accordance with said structure-activity models, reagents from a reagent database that, when combined, will produce a set of compounds predicted to exhibit activity/properties more closely matching said prescribed set of activity/properties; and synthesis instruction generating means for generating synthesis instructions that, when executed, enable synthesis by said system of said set of compounds.

11. The synthesis protocol generator of claim 10, further comprising:

comparing means for comparing said structure-activity data of said chemical compounds against said prescribed set of activity/properties to identify any of said chemical compounds substantially conforming to said prescribed set of activity/properties; and classifying means for classifying said identified chemical compounds as lead compounds.

12. The synthesis protocol generator of claim 10, wherein said reagent identifying means comprises:

means for identifying, in accordance with said structure-activity models, reagents from said reagent database that, when combined, will produce a second set of compounds predicted to have a superior ability to validate said structure-activity models, wherein said first and second sets of compounds are not mutually exclusive;

wherein said synthesis instruction generating means comprises:

means for generating synthesis instructions that, when executed, enable synthesis of said second set of compounds.

13. The synthesis protocol generator of claim 10, wherein said reagent identifying means comprises:

means for identifying, in accordance with said structure-activity models, reagents from said reagent database that, when combined, will produce a second set of compounds predicted to have a superior ability to discriminate between said structure-activity models, wherein said first and second sets of compounds are not mutually exclusive;

wherein said synthesis instruction generating means comprises:

means for generating synthesis instructions that, when executed, enable synthesis of said second set of compounds.

14. The synthesis protocol generator of claim 10, wherein said reagent identifying means comprises:

means for identifying, in accordance with said structure-activity models, reagents from said reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;

wherein said synthesis instruction generating means comprises:

means for generating synthesis instructions that, when executed, enable synthesis of said second and third set of compounds.

15. The synthesis protocol generator of claim 10, wherein said reagent identifying means comprises:

means for identifying, in accordance with said structure-activity models, reagents from said reagent database that, when combined, will produce a second set of compounds predicted to have superior three-dimensional receptor fit, wherein said first and second sets of compounds are not mutually exclusive;

wherein said synthesis instruction generating means comprises:

means for generating synthesis instructions that, when executed, enable synthesis of said second set of compounds.

16. The synthesis protocol generator of claim 10, wherein said reagent identifying means comprises:

means for identifying reagents from said reagent database that, when combined, will produce a second set of compounds with structural, physical, or chemical characteristics similar to characteristics of compounds in a structure-activity database whose activity/properties most closely conform to said prescribed set of activity/properties, wherein said first and second sets of compounds are not mutually exclusive;

wherein said synthesis instruction generating means comprises:

means for generating synthesis instructions that, when executed, enable synthesis of said second set of compounds.

17. The synthesis protocol generator of claim 10, further comprising:
   means for generating a list of potential chemical compounds to possibly synthesize, each of said potential chemical compounds comprising N of said reagents identified by said reagent identifying means; and
   candidate compound identifying means for selecting from said list of potential chemical compounds a plurality of candidate compounds that are suitable for synthesis.

18. The synthesis protocol generator of claim 17, wherein said synthesis protocol generator further comprises:
   optimal set selecting means for selecting an optimal set of said candidate compounds to synthesize based on at least one of the following factors:
      (I) their respective predicted abilities to exhibit activity/properties more closely matching said prescribed set of activity/properties as indicated by said structure-activity models;
      (ii) their respective predicted abilities to validate said structure-activity models;
      (iii) their respective predicted abilities to discriminate between said structure-activity models;
      (iv) their respective predicted abilities to have superior three-dimensional receptor fit; and
      (v) similarity between their respective structural, physical, or chemical characteristics and characteristics of compounds in a structure-activity database whose activity/properties most closely conform to said prescribed set of activity/properties.

19. The synthesis protocol generator of claim 18, wherein said optimal set selecting means comprises:
   means for selecting said optimal set by individually ranking said candidate compounds based on at least one of factors (I)–(v).

20. The synthesis protocol generator of claim 18, wherein said optimal set selecting means comprises:
   means for selecting said optimal set by ranking combinations of said candidate compounds based on at least one of factors (I)–(v).

21. A computer assisted method for aiding in generating compounds having a prescribed set of activity/properties, said method comprising the steps of:
   (1) analyzing structure-activity data of compounds contained in a directed diversity chemical library and historical structure-activity data pertaining to compounds synthesized and analyzed in the past to derive structure-activity models having enhanced predictive and discriminating capabilities;
   (2) identifying, in accordance with said structure-activity models, reagents from a reagent database that, when combined, will produce a set of compounds predicted to exhibit activity/properties more closely matching said prescribed set of activity/properties; and (3) generating synthesis instructions that, when executed, enable synthesis of said set of compounds.

22. The method of claim 21, further comprising the steps of:
   (4) comparing said structure-activity data of said chemical compounds against said prescribed set of activity/properties to identify any of said chemical compounds substantially conforming to said prescribed set of activity/properties; and
   (5) classifying said identified chemical compounds as lead compounds.

23. The method of claim 21, wherein step (2) comprises the steps of:
   identifying, in accordance with said structure activity models, reagents from said reagent database that, when combined, will produce a second set of compounds predicted to have a superior ability to validate said structure-activity models, wherein said first and second sets of compounds are not mutually exclusive;
   wherein step (3) comprises the step of:
      generating synthesis instructions that, when executed, enable synthesis of said second set of compounds.

24. The method of claim 21, wherein step (2) comprises the steps of:
   identifying, in accordance with said structure-activity models, reagents from said reagent database that, when combined, will produce a second set of compounds predicted to have a superior ability to discriminate between said structure-activity models, wherein said first and second sets of compounds are not mutually exclusive;
   wherein step (3) comprises the step of:
      generating synthesis instructions that, when executed, enable synthesis of said second set of compounds.

25. The method of claim 21, wherein step (2) comprises the steps of:
   identifying, in accordance with said structure-activity models, reagents from said reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;
   wherein step (3) comprises the step of:
      generating synthesis instructions that, when executed, enable synthesis of said second and third set of compounds.

26. The method of claim 21, wherein step (2) comprises the steps of:
   identifying, in accordance with said structure-activity models, reagents from said reagent database that, when combined, will produce a second set of compounds predicted to have superior three-dimensional receptor fit, wherein said first and second sets of compounds are not mutually exclusive;
   wherein step (3) comprises the step of:
      generating synthesis instructions that, when executed, enable synthesis of said second set of compounds.

27. The method of claim 21, wherein step (2) comprises the steps of:
   identifying reagents from said reagent database that, when combined, will produce a second set of compounds with structural, physical, or chemical characteristics similar to characteristics of compounds in a structure-activity database whose activity/properties most closely conform to said prescribed set of activity/properties, wherein said first and second sets of compounds are not mutually exclusive;
   wherein step (3) comprises the step of:
      generating synthesis instructions that, when executed, enable synthesis of said second set of compounds.

28. The method of claim 21, further comprising the steps of:
   generating a list of potential chemical compounds to possibly synthesize, each of said potential chemical compounds comprising N of said reagents identified by said reagent identifying means; and selecting from said list of potential chemical compounds a plurality of candidate compounds that are suitable for synthesis.

29. The method of claim 28, further comprising the steps of:

selecting an optimal set of said candidate compounds to synthesize based on at least one of the following factors:
(I) their respective predicted abilities to exhibit activity/properties more closely matching said prescribed set of activity/properties as indicated by said structure-activity models;
(ii) their respective predicted abilities to validate said structure-activity models;
(iii) their respective predicted abilities to discriminate between said structure-activity models;
(iv) their respective predicted abilities to have superior three-dimensional receptor fit; and
(v) similarity between their respective structural, physical, or chemical characteristics and characteristics of compounds in a structure-activity database whose activity/properties most closely conform to said prescribed set of activity/properties.

30. A computer program product comprising a computer useable medium having computer program logic recorded thereon for enabling a processor to assist in generating compounds having a prescribed set of activity/properties, said computer program logic comprising:

structure-activity model derivation means for enabling the processor to analyze structure-activity data of compounds in a directed diversity chemical library and historical structure-activity data pertaining to compounds synthesized and analyzed in the past to derive structure-activity models having enhanced predictive and discriminating capabilities;

reagent identifying means for enabling the processor to identify, in accordance with said structure-activity models, reagents from a reagent database that, when combined, will produce a set of compounds predicted to exhibit activity/properties more closely matching said prescribed set of activity/properties; and synthesis instruction generating means for enabling the processor to generate synthesis instructions that, when executed, enable synthesis of said set of compounds.

31. The computer program product of claim 30, wherein said computer program logic further comprises:

comparing means for enabling the processor to compare said structure-activity data of said chemical compounds against said prescribed set of activity/properties to identify any of said chemical compounds conforming to said prescribed set of activity/properties; and classifying means for enabling the processor to classify said identified chemical compounds as chemical compounds of potential interest.

32. The computer program product of claim 30, wherein said reagent identifying means comprises:

means for enabling the processor to identify, in accordance with said structure-activity models, reagents from said reagent database that, when combined, will produce a second set of compounds predicted to have a superior ability to validate said structure-activity models, wherein said first and second sets of compounds are not mutually exclusive;

wherein said synthesis instruction generating means comprises:

means for enabling the processor to generate synthesis instructions that, when executed, enable synthesis of said second set of compounds.

33. The computer program product of claim 30, wherein said reagent identifying means comprises:

means for enabling the processor to identify, in accordance with said structure-activity models, reagents from said reagent database that, when combined, will produce a second set of compounds predicted to have a superior ability to discriminate between said structure-activity models, wherein said first and second sets of compounds are not mutually exclusive;

wherein said synthesis instruction generating means comprises:

means for enabling the processor to generate synthesis instructions that, when executed, enable synthesis of said second set of compounds.

34. The computer program product of claim 30, wherein said reagent identifying means comprises:

means for enabling the processor to identify, in accordance with said structure-activity models, reagents from said reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;

wherein said synthesis instruction generating means comprises:

means for enabling the processor to generate synthesis instructions that, when executed, enable synthesis of said second and third set of compounds.

35. The computer program product of claim 30, wherein said reagent identifying means comprises:

means for enabling the processor to identify, in accordance with said structure-activity models, reagents from said reagent database that, when combined, will produce a second set of compounds predicted to have superior three-dimensional receptor fit, wherein said first and second sets of compounds are not mutually exclusive;

wherein said synthesis instruction generating means comprises:

means for enabling the processor to generate synthesis instructions that, when executed, enable synthesis of said second set of compounds.

36. The computer program product of claim 30, wherein said reagent identifying means comprises:

means for enabling the processor to identify reagents from said reagent database that, when combined, will produce a second set of compounds with structural, physical, or chemical characteristics similar to characteristics of compounds in a structure-activity database whose activity/properties most closely conform to said prescribed set of activity/properties, wherein said first and second sets of compounds are not mutually exclusive;

wherein said synthesis instruction generating means comprises:

means for enabling the processor to generate synthesis instructions that, when executed, enable synthesis of said second set of compounds.

37. The computer program product of claim 30, wherein said computer program logic further comprises:

means for enabling the processor to generate a list of potential chemical compounds to possibly synthesize, each of said potential chemical compounds comprising N of said reagents identified by said reagent identifying means; and candidate compound identifying means for enabling the processor to select from said list of potential chemical compounds a plurality of candidate compounds that are suitable for synthesis.

38. The computer program product of claim 37, wherein said computer program logic further comprises:

optimal set selecting means for enabling the processor to select an optimal set of said candidate compounds to synthesize based on at least one of the following factors:
(I) their respective predicted abilities to exhibit activity/properties more closely matching said prescribed set of activity/properties as indicated by said structure-activity models;
(II) their respective predicted abilities to validate said structure-activity models;
(III) their respective predicted abilities to discriminate between said structure-activity models;
(IV) their respective predicted abilities to have superior three-dimensional receptor fit; and
(V) similarity between their respective structural, physical, or chemical characteristics and characteristics of compounds in a structure-activity database whose activity/properties most closely conform to said prescribed set of activity/properties.

39. The computer program product of claim 38, wherein said optimal set selecting means comprises:

means for enabling the processor to select said optimal set by individually ranking said candidate compounds based on at least one of factors (I)–(V).

40. The computer program product of claim 38, wherein said optimal set selecting means comprises:

means for enabling the processor to select said optimal set by ranking combinations of said candidate compounds based on at least one of factors (I)–(V).

41. A computer assisted system for at least partially automatically generating compounds having a prescribed set of properties, comprising:

synthesizing means for synthesizing, in accordance with synthesis instructions, a directed diversity chemical library comprising a plurality of chemical compounds;

chemical compound analyzing means for analyzing said chemical compounds to obtain structure-activity data pertaining thereto;

comparing means for comparing said structure-activity data of said chemical compounds against said prescribed set of properties to identify any of said chemical compounds conforming to said prescribed set of properties;

structure-activity analyzing means for analyzing said structure-activity data of said compounds and historical structure-activity data pertaining to compounds synthesized and analyzed in the past to derive structure-activity models having enhanced predictive and discriminating capabilities;

reagent identifying means for identifying, in accordance with said structure-activity models, reagents from a reagent database that, when combined, will produce a set of compounds predicted to exhibit activity/properties more closely matching said prescribed set of properties; and synthesis instructions generating means for generating synthesis instructions that, when performed, enable synthesis of said set of compounds.

42. The system of claim 41, wherein said reagent identifying means comprises:

means for identifying reagents from a reagent database that, when combined, will produce a second set of compounds predicted to have a superior ability to validate said structure-activity models, wherein said first and second sets of compounds are not mutually exclusive;

wherein said synthesis instructions generating means comprises means for generating synthesis instructions that, when performed, enable synthesis of said second set of compounds.

43. The system of claim 41, wherein said reagent identifying means comprises:

means for identifying reagents from a reagent database that, when combined, will produce a second set of compounds predicted to have a superior ability to discriminate between said structure-activity models, wherein said first and second sets of compounds are not mutually exclusive;

wherein said synthesis instructions generating means comprises means for generating synthesis instructions that, when performed, enable synthesis of said second set of compounds.

44. The system of claim 41, wherein said reagent identifying means comprises:

means for identifying reagents from a reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;

wherein said synthesis instructions generating means comprises means for generating synthesis instructions that, when performed, enable synthesis of said second and third set of compounds.

45. The system of claim 41, wherein said reagent identifying means comprises:

means for identifying reagents from a reagent database that, when combined, will produce a second set of compounds predicted to have superior three-dimensional receptor fit, wherein said first and second sets of compounds are not mutually exclusive;

wherein said synthesis instructions generating means comprises means for generating synthesis instructions that, when performed, enable synthesis of said second set of compounds.

46. The system of claim 41, wherein said reagent identifying means operates according to operator input.

47. The system of claim 41, wherein said synthesis instructions generating means comprises:

means for receiving operator input pertaining to the generation of said synthesis instructions; and means for generating said synthesis instructions based, at least in part, on said operator input.

48. A computer program product comprising a computer useable medium having computer program logic recorded thereon for enabling a processor in a computer to at least partially automatically generate compounds having a prescribed set of properties, said computer program logic comprising:

synthesizing means for enabling the processor to synthesize, in accordance with synthesis instructions, a directed diversity chemical library comprising a plurality of chemical compounds;

chemical compound analyzing means for enabling the processor to analyze said chemical compounds to obtain structure-activity data pertaining thereto;

comparing means for enabling the processor to compare said structure-activity data of said chemical compounds against said prescribed set of properties to identify any of said chemical compounds conforming to said prescribed set of properties;

structure-activity analyzing means for enabling the processor to analyze said structure-activity data of said compounds and historical structure-activity data pertaining to compounds synthesized and analyzed in the past to derive structure-activity models having enhanced predictive and discriminating capabilities;

reagent identifying means for enabling the processor to identify, in accordance with said structure-activity models, reagents from a reagent database that, when combined, will produce a set of compounds predicted to exhibit activity/properties more closely matching said prescribed set of properties; and synthesis instructions generating means for enabling the processor to generate synthesis instructions that, when performed, enable synthesis of said set of compounds.

49. The computer program product of claim 48, wherein said reagent identifying means comprises:

means for enabling the processor to identify reagents from a reagent database that, when combined, will produce a second set of compounds predicted to have a superior ability to validate said structure-activity models, wherein said first and second sets of compounds are not mutually exclusive;

wherein said synthesis instructions generating means comprises means for enabling the processor to generate synthesis instructions that, when performed, enable synthesis of said second set of compounds.

50. The computer program product of claim 48, wherein said reagent identifying means comprises:

means for enabling the processor to identify reagents from a reagent database that, when combined, will produce a second set of compounds predicted to have a superior ability to discriminate between said structure-activity models, wherein said first and second sets of compounds are not mutually exclusive;

wherein said synthesis instructions generating means comprises means for enabling the processor to generate synthesis instructions that, when performed, enable synthesis of said second set of compounds.

51. The computer program product of claim 48, wherein said reagent identifying means comprises;

means for enabling the processor to identify reagents from a reagent database that, when combined, will produce a second set of compounds predicted to have a superior ability to validate said structure-activity models, and a third set of compounds predicted to have a superior ability to discriminate between said structure-activity models, wherein said first, second, and third sets of compounds are not mutually exclusive;

wherein said synthesis instructions generating means comprises means for enabling the processor to generate synthesis instructions that, when performed, enable synthesis of said second and third set of compounds.

52. The computer program product of claim 48, wherein said reagent identifying means comprises:

means for enabling the processor to identify reagents from a reagent database that, when combined, will produce a second set of compounds predicted to have superior three-dimensional receptor fit, wherein said first and second sets of compounds are not mutually exclusive;

wherein said synthesis instructions generating means comprises means for enabling the processor to generate synthesis instructions that, when performed, enable synthesis of said second set of compounds.

53. The computer program product of claim 48, wherein said reagent identifying means operates according to operator input.

54. The computer program product of claim 48, wherein said synthesis instructions generating means comprises:

means for enabling the processor to receive operator input pertaining to the generation of said synthesis instructions; and means for enabling the processor to generate said synthesis instructions based, at least in part, on said operator input.

* * * * *